United States Patent
Almeida et al.

(10) Patent No.: US 10,047,361 B2
(45) Date of Patent: *Aug. 14, 2018

(54) DISULFIDE-CONTAINING ALKYNE LINKING AGENTS

(71) Applicant: Arrowhead Pharmaceuticals, Inc., Pasadena, CA (US)

(72) Inventors: Aaron Almeida, Madison, WI (US); Andrei V. Blokhin, Fitchburg, WI (US); Darren H. Wakefield, Fitchburg, WI (US); Jonathan D. Benson, Stoughton, WI (US); David B. Rozema, Cross Plains, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/716,809

(22) Filed: Sep. 27, 2017

(65) Prior Publication Data
US 2018/0023084 A1 Jan. 25, 2018

Related U.S. Application Data

(63) Continuation of application No. 15/071,395, filed on Mar. 16, 2016, now Pat. No. 9,803,201.

(60) Provisional application No. 62/235,860, filed on Oct. 1, 2015, provisional application No. 62/168,244, filed on May 29, 2015, provisional application No. 62/134,186, filed on Mar. 17, 2015.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/14* (2013.01); *C12N 2310/315* (2013.01); *C12N 2310/321* (2013.01); *C12N 2310/3515* (2013.01); *C12N 2310/3521* (2013.01); *C12N 2310/3533* (2013.01); *C12N 2320/50* (2013.01)

(58) Field of Classification Search
None
See application file for complete search history.

(56) References Cited

U.S. PATENT DOCUMENTS

| | | | |
|---|---|---|---|
| 7,375,234 B2 | 5/2008 | Sharpless et al. | |
| 8,084,599 B2 | 12/2011 | Rossi et al. | |
| 8,349,809 B2 | 1/2013 | Brown | |
| 8,513,207 B2 | 8/2013 | Brown | |
| 2009/0068738 A1 | 3/2009 | Bertozzi et al. | |
| 2012/0029186 A1 | 2/2012 | Popik et al. | |
| 2012/0230938 A1 | 9/2012 | Rozema et al. | |
| 2015/0045573 A1 | 2/2015 | Cheng et al. | |

FOREIGN PATENT DOCUMENTS

| | | |
|---|---|---|
| WO | 2009067663 A1 | 5/2009 |
| WO | 2009082606 A2 | 7/2009 |
| WO | 2011136645 A1 | 11/2011 |
| WO | 2012128868 A2 | 9/2012 |
| WO | 2014134483 A2 | 9/2014 |
| WO | 2014189370 A1 | 11/2014 |

OTHER PUBLICATIONS

U.S. Appl. No. 15/071,395, filed Sep. 2016, Almeida; Aaron.*
Amarzguioui et al. "An algorithm for selection of functional siRNA sequences" Biochemical and Biophysical Research Communications 2004 vol. 316, p. 1050-1058.
Chalk et al. "Improved and automated prediction of effective siRNA" Biochemical and Biophysical Research Communications 2004 vol. 319, p. 264-274.
Heale et al. "siRNA target site secondary structure predictions using local stable substructures" Nucleic Acids Research (2005) 33(3).
Khvorova et al. "Functional siRNAs and miRNAs Exhibit Strand Bias" Cell 2003 vol. 115, p. 209-216.
Pei et al. "On the art of identifying effective and specific siRNAs" Nature Methods 2006 vol. 3(9), p. 670-676.
Reynolds et al. "Targeting the cancer stroma with a fibroblast activation protein-activated promelittin protoxin" Nature Biotechnology 2004.
Schwarz et al. "Asymmetry in the Assembly of the RNAi Enzyme Complex" Cell 2003 vol. 115, p. 199-208.
Ui-Tei et al. "Guidelines for the selection of highly effective siRNA sequences for mammalian and chick RNA Interference" Nucleic Acids Research 2004 vol. 32(3)936-948.
Jewett et al.; "Rapid Cu-Free Click Chemistry with Readily Synthesized Biarylazacyclooctynones"; J. Am. Chem. Soc.; 2010; 132 (11); pp. 3688-3690.
Gordon et al.; "Reactivity of Biarylazacyclooctynones in Copper-Free Click Chemistry"; J. Am. Chem. Soc.; 2012; 134 (22); pp. 9199-9208.
Starke et al.; "A novel dibenzo-azacyclooctyne precursor for application in regioselective copper-Free click chemistry, obtained by an innovative 3-step synthesis"; Arkivoc; 2010; xi: 350-359.
Banerjee et al.; "Targeted and armed oncolytic adenovirus via chemoselective modification"; Bioorganic & Medicinal Chemistry Letters; 2011; 21(17): 4985-4988.
Chigrinova, M. et al.; :Rearrangements and addition reactions of biarylazacyclooctynones and the implications to copper-free click chemistry; Organic & Biomolecular Chemistry; 2013; 11(21): 3436-3441.
Debets, MF. et al.; "Aza-dibenzoycclooctynes for fast and efficient enzyme PEGylation via copper-free (3+2) cycloaddition" Chem. Commun.; 2010; 46(1): 97-99.
Carroll et al.; "Enhanced Stability in Vitro and in Vivo of Immunoconjugates Prepared with 5-Methyl-2- minothiolane"; Bioconjugate Chem.; 1994; 248-256.

(Continued)

*Primary Examiner* — Michael Barker
(74) *Attorney, Agent, or Firm* — Robert Michael Teigen

(57) ABSTRACT

Described are improved disulfide-containing alkyne linking agents having have branched disulfides. The improved linking agents exhibit improved stability. The linking agents are useful for attachment of oligonucleotides to targeting groups or delivery agents.

12 Claims, 12 Drawing Sheets

(56) References Cited

OTHER PUBLICATIONS

Widdison et al.; "Semisynthetic Maytansine Analogues for the Targeted Treatment of Cancer"; J. Med. Chem.; 2006; 49; 4392-4408.

Murty, S et al.; "Nanoparticles functionalized with collagenase exhibit improved tumor accumulation in a murine xenograft model"; Particle and Particle Systems Characterization; vol. 31; No. 12; Dec. 2014; pp. 1307-1312; p. 9, figure 1B.

International Search Report and Written Opinion of the International Searching Authority for corresponding Application No. PCT/US16/22560 dated Jun. 14, 2016.

* cited by examiner

SEQUENCE LISTING

<160> NUMBER OF SEQ ID NOS: 10

<210> SEQ ID NO 1
<211> LENGTH: 21
<212> TYPE: DNA
<213> ORGANISM: artificial sequence
<220> FEATURE:
<223> OTHER INFORMATION: antisense strand of an RNAi agent
<220> FEATURE:
<221> NAME/KEY: modified_base
<222> LOCATION: 2-19
<223> OTHER INFORMATION: /mod_base = "2'-hydroxy corresponding nucleoside"

<400> SEQUENCE: 1
tgaguuggca cgccuuugct t                                              21

<210> SEQ ID NO 2
<211> LENGTH: 20
<212> TYPE: DNA
<213> ORGANISM: artificial sequence
<220> FEATURE:
<223> OTHER INFORMATION: sense strand of an RNAi agent
<220> FEATURE:
<221> NAME/KEY: modified_base
<222> LOCATION: 1-19
<223> OTHER INFORMATION: /mod_base = "2'-hydroxy corresponding nucleoside"

<400> SEQUENCE: 2
gcaaaggcgu gccaacucat                                                20

<210> SEQ ID NO 3
<211> LENGTH: 21
<212> TYPE: DNA
<213> ORGANISM: artificial sequence
<220> FEATURE:
<223> OTHER INFORMATION: antisense strand of an RNAi agent
<220> FEATURE:
<221> NAME/KEY: modified_base
<222> LOCATION: 2-19
<223> OTHER INFORMATION: /mod_base = "2'-hydroxy corresponding nucleoside"

<400> SEQUENCE: 3
tgaguuggca cgccuuugct t                                              21

<210> SEQ ID NO 4
<211> LENGTH: 20
<212> TYPE: DNA
<213> ORGANISM: artificial sequence
<220> FEATURE:
<223> OTHER INFORMATION: sense strand of an RNAi agent
<220> FEATURE:
<221> NAME/KEY: modified_base
<222> LOCATION: 1-19
<223> OTHER INFORMATION: /mod_base = "2'-hydroxy corresponding nucleoside"

<400> SEQUENCE: 4
gcaaaggcgu gccaacucat                                                20

<210> SEQ ID NO 5
<211> LENGTH: 21
<212> TYPE: DNA
<213> ORGANISM: artificial sequence
<220> FEATURE:
<223> OTHER INFORMATION: antisense strand of an RNAi agent
<220> FEATURE:
<221> NAME/KEY: modified_base

```
<222> LOCATION: 2-19
<223> OTHER INFORMATION: /mod_base = "2'-hydroxy corresponding
      nucleoside"

<400> SEQUENCE: 5
tgaguuggca cgccuuugct t                                              21

<210> SEQ ID NO 6
<211> LENGTH: 20
<212> TYPE: DNA
<213> ORGANISM: artificial sequence
<220> FEATURE:
<223> OTHER INFORMATION: sense strand of an RNAi agent
<220> FEATURE:
<221> NAME/KEY: modified_base
<222> LOCATION: 1-19
<223> OTHER INFORMATION: /mod_base = "2'-hydroxy corresponding
      nucleoside"

<400> SEQUENCE: 6
gcaaaggcgu gccaacucat                                                20

<210> SEQ ID NO 7
<211> LENGTH: 21
<212> TYPE: DNA
<213> ORGANISM: artificial sequence
<220> FEATURE:
<223> OTHER INFORMATION: antisense strand of an RNAi agent
<220> FEATURE:
<221> NAME/KEY: modified_base
<222> LOCATION: 2-19
<223> OTHER INFORMATION: /mod_base = "2'-hydroxy corresponding
      nucleoside"

<400> SEQUENCE: 7
tgaguuggca cgccuuugct t                                              21

<210> SEQ ID NO 8
<211> LENGTH: 20
<212> TYPE: DNA
<213> ORGANISM: artificial sequence
<220> FEATURE:
<223> OTHER INFORMATION: sense strand of an RNAi agent
<220> FEATURE:
<221> NAME/KEY: modified_base
<222> LOCATION: 1-19
<223> OTHER INFORMATION: /mod_base = "2'-hydroxy corresponding
      nucleoside"

<400> SEQUENCE: 8
gcaaaggcgu gccaacucat                                                20

<210> SEQ ID NO 9
<211> LENGTH: 21
<212> TYPE: DNA
<213> ORGANISM: artificial sequence
<220> FEATURE:
<223> OTHER INFORMATION: antisense strand of an RNAi agent
<220> FEATURE:
<221> NAME/KEY: modified_base
<222> LOCATION: 2-19
<223> OTHER INFORMATION: /mod_base = "2'-hydroxy corresponding
      nucleoside"

<400> SEQUENCE: 9
tgaguuggca cgccuuugct t                                              21

<210> SEQ ID NO 10
<211> LENGTH: 20
```

```
<212> TYPE: DNA
<213> ORGANISM: artificial sequence
<220> FEATURE:
<223> OTHER INFORMATION: sense strand of an RNAi agent
<220> FEATURE:
<221> NAME/KEY: modified_base
<222> LOCATION: 1-19
<223> OTHER INFORMATION: /mod_base = "2'-hydroxy corresponding
      nucleoside"

<400> SEQUENCE: 10
gcaaaggcgu gccaacucat                                          20
```

DISULFIDE-CONTAINING ALKYNE LINKING AGENTS

BACKGROUND

Synthetic oligonucleotides, such as antisense molecules, aptamers, ribozymes and RNA interference (RNAi) molecules, are increasingly used in biomedical research, diagnostics and therapeutics. These synthetic oligonucleotides have been used to inhibit or knock-down expression of a gene in vitro, in situ, and in vivo in a sequence dependent manner.

It is frequently useful to attach or link targeting ligands or other pharmacological modifiers to synthetic oligonucleotides, especially for therapeutic in vivo delivery. To be useful, the linkage chemistry should be modular, so that it is readily adaptable to different synthetic oligonucleotides as well as different targeting ligands and pharmacological modifiers. In addition, the linkage chemistry should have simple reaction conditions, be efficient (i.e. give high chemical yields), not require toxic or other detrimental products, and not produce toxic or other detrimental byproducts. The linkage chemistry should also be stable outside of the target cell, such as in circulation, subcutaneous space, or extracellular space, but be readily cleavable at the final site of action, such as inside the target cell.

An example of such a reaction useful in linking synthetic oligonucleotides to targeting ligands or other pharmacological modifiers is the cycloaddition of cyclic alkynes and azides, which is one of the reactions known as "click reactions" or "click chemistry". In click reactions, two separate molecular entities, one charged with an azide and one charged with a strained cycloalkyne, will spontaneously combine into a single molecule by a reaction called strain-promoted azide-alkyne cycloaddition (SPAAC). The reaction is mild in nature, rapid, and high-yielding and occurs at about physiological pH, in water, and in the vicinity of biomolecular functionalities. This reaction has become a versatile tool for bioorthogonal labeling and imaging of biomolecules (e.g. proteins, lipids, glycans and the like), proteomics and materials science. The cycloaddition reaction proceeds spontaneously, in the absence of a catalyst. Metal-free cycloadditions are also referred to as "metal-free click reactions". The power of SPAAC for bioorthogonal labeling lies in the fact that an isolated cyclic alkyne or azide is fully inert to biological functionalities, such as for example amines, thiols, acids or carbonyls, but in combination undergoes rapid and irreversible cycloaddition, leading to a stable triazole conjugate. For example, azido-modified proteins, obtained by expression in auxotrophic bacteria, genetic engineering or chemical conversion, can be cleanly labeled with biotin, fluorophores, PEG-chains or other functionalities upon simply stirring the azido-protein with a cyclooctyne conjugate. Moreover, the small size of azide has proven highly useful for application of SPAAC in the imaging of specific biomolecules by means of the chemical reporter strategy.

We have found the alkyne disulfides currently available, such as Dibenzocyclooctyne (DBCO)—S—S—NHS,

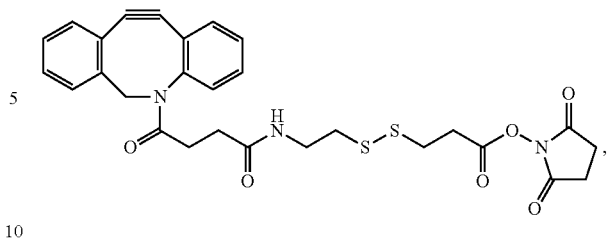

offer insufficient stability during modification of compounds leading to poor synthetic yields and the presence of undesired impurities. We now describe improved alkyne disulfides having improved stability properties resulting in improved yields and purity.

SUMMARY

Described herein are cyclooctyne-alkyl disulfide compounds having the structure represented by:

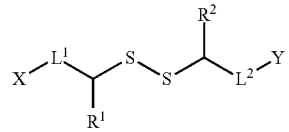

wherein $R^1$ and/or $R^2$ are alkyl groups, $L^1$ and $L^2$ are linkers, X is a cyclooctyne, and Y comprises a reactive group, synthetic oligonucleotide, or RNAi agent. In some embodiments, $R^1$ is an alkyl group and $R^2$ is a hydrogen. In some embodiments, $R^2$ is an alkyl group and $R^1$ is a hydrogen. In some embodiments, the alkyl group is a methyl group or ethyl group. In some embodiments, Y comprises an RNAi agent.

Described herein are cyclooctyne-alkyl disulfide compounds having the structure represented by:

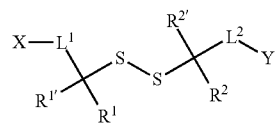

wherein $R^1$, $R^{1'}$, $R^2$ and/or $R^{2'}$ are alkyl groups, X comprises a cyclooctyne, and Y comprises a reactive group or a synthetic oligonucleotide. In some embodiments, $R^1$ and $R^{1'}$ are alkyl groups and $R^2$ and $R^{2'}$ are hydrogens. In some embodiments, $R^2$ and $R^{2'}$ are alkyl groups and $R^1$ and $R^{1'}$ are hydrogens. In some embodiments, $R^1$, $R^{1'}$, $R^2$, and $R^{2'}$ are alkyl groups. In some embodiments, $R^1$ is an alkyl groups and $R^{1'}$, $R^2$, and $R^{2'}$ are hydrogens. In some embodiments, $R^{1'}$ are alkyl groups and $R^1$, $R^2$, and $R^{2'}$ are hydrogens. In some embodiments, $R^2$ are alkyl groups and $R^1$, $R^{1'}$, and $R^{2'}$ are hydrogens. In some embodiments, $R^{2'}$ are alkyl groups and $R^1$, $R^{1'}$, and $R^2$ are hydrogens. In some embodiments, $R^1$, $R^{1'}$, and $R^2$ are alkyl groups $R^{2'}$ is a hydrogen. In some embodiments, $R^1$, $R^{1'}$, and $R^{2'}$ are alkyl groups $R^2$ is a hydrogen. In some embodiments, $R^1$, $R^2$, and $R^{2'}$ are alkyl groups $R^{1'}$ is a hydrogen. In some embodiments, $R^{1'}$, $R^2$, and $R^{2'}$ are alkyl groups $R^1$ is a hydrogen. In some embodiments, the alkyl groups are methyl groups. In some embodiments, Y comprises an RNAi agent.

Described herein are cyclooctyne-alkyl disulfide compounds having the structure represented by:

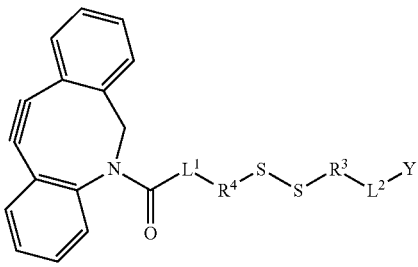

wherein $R^3$ is $C(R^5R^6)$ wherein $R^5$ is hydrogen, methyl or ethyl, and $R^6$ is hydrogen, methyl or ethyl, $R^4$ is $C(R^7R^8)$ wherein $R^7$ is hydrogen, methyl or ethyl, and $R^8$ is hydrogen, methyl or ethyl, at least one of $R^5$, $R^6$, $R^7$, and $R^8$ is methyl or ethyl, $L^1$ is a first linker, $L^2$ is a second linker, and Y comprises a reactive group, synthetic oligonucleotide or RNAi agent. In some embodiments, $R^5$ or $R^6$ is methyl or ethyl and $R^7$ and $R^8$ are both hydrogen. In some embodiments, $R^7$ or $R^8$ is methyl or ethyl, and $R^5$ and $R^6$ are both hydrogen. In some embodiments, $R^5$ is $CH_3$, and $R^6$, $R^7$ and $R^8$ are each hydrogen. In some embodiments, $R^7$ is $CH_3$, and $R^5$, $R^6$ and $R^8$ are each hydrogen. In some embodiments, Y comprises an RNAi agent.

Described herein are cyclooctyne-alkyl disulfide compounds having the structure represented by:

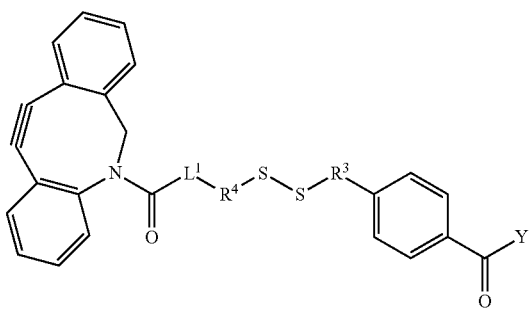

wherein $R^3$ is $C(R^5R^6)$ wherein $R^5$ is hydrogen, methyl or ethyl, and $R^6$ is hydrogen, methyl or ethyl, $R^4$ is $C(R^7R^8)$ wherein $R^7$ is hydrogen, methyl or ethyl, and $R^8$ is hydrogen, methyl or ethyl, at least one of $R^5$, $R^6$, $R^7$, and $R^8$ is methyl or ethyl, $L^1$ is a linker, and Y comprises a reactive group, synthetic oligonucleotide or RNAi agent. In some embodiments, $R^5$ or $R^6$ is methyl or ethyl, and $R^7$ and $R^8$ are both hydrogen. In some embodiments, $R^7$ or $R^8$ is methyl or ethyl, and $R^5$ and $R^6$ are both hydrogen. In some embodiments, $R^5$ is $CH_3$, and $R^6$, $R^7$ and $R^8$ are each hydrogen. In some embodiments, $R^7$ is $CH_3$, and $R^5$, $R^6$ and $R^8$ are each hydrogen. In some embodiments, Y comprises an RNAi agent.

Described herein are compounds having the structures represented by:

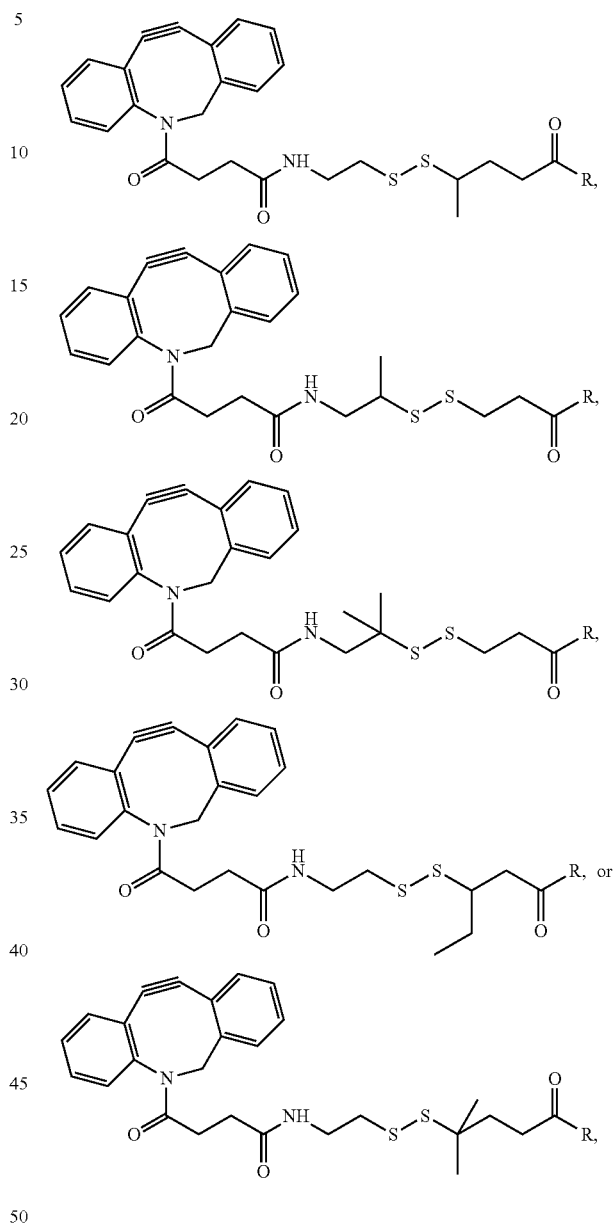

wherein R is a reactive group, NHS reactive group, synthetic oligonucleotide, or RNAi agent.

Described herein are compounds having the structure represented by:

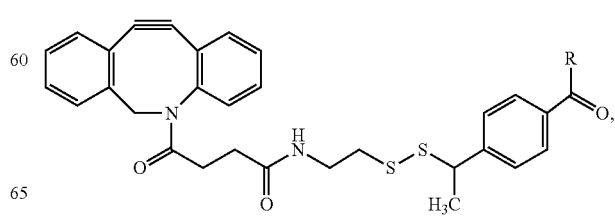

-continued

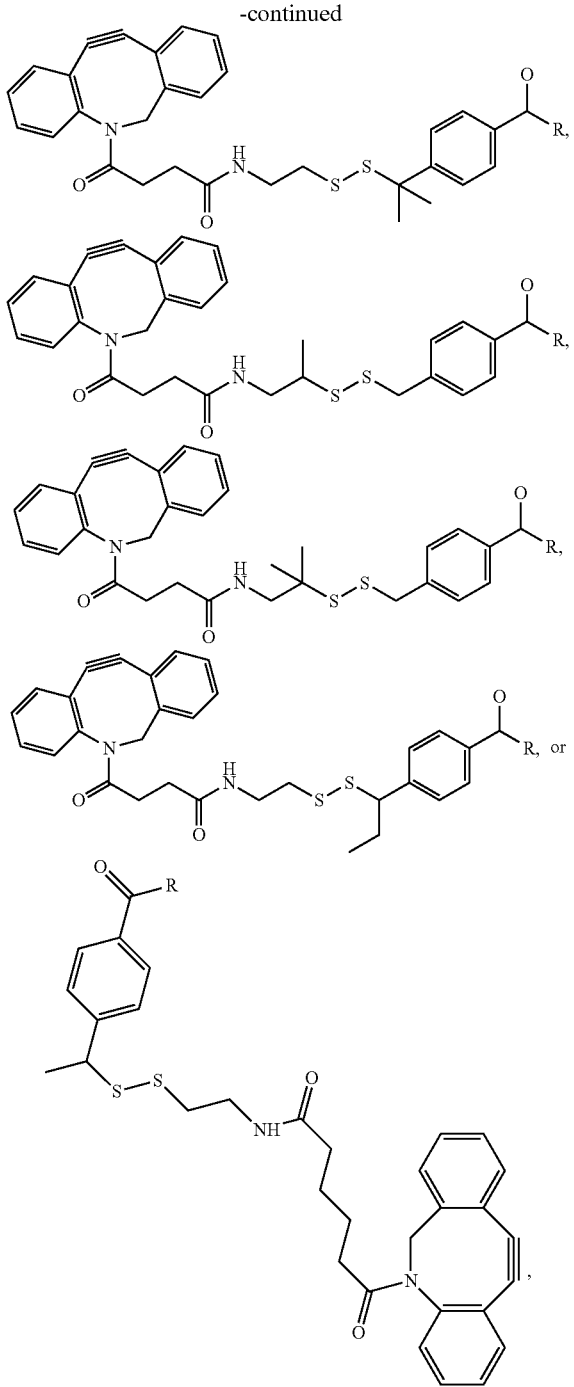

wherein R comprises a reactive group, NHS reactive group, synthetic oligonucleotide, or RNAi agent.

DETAILED DESCRIPTION

Figure 1:
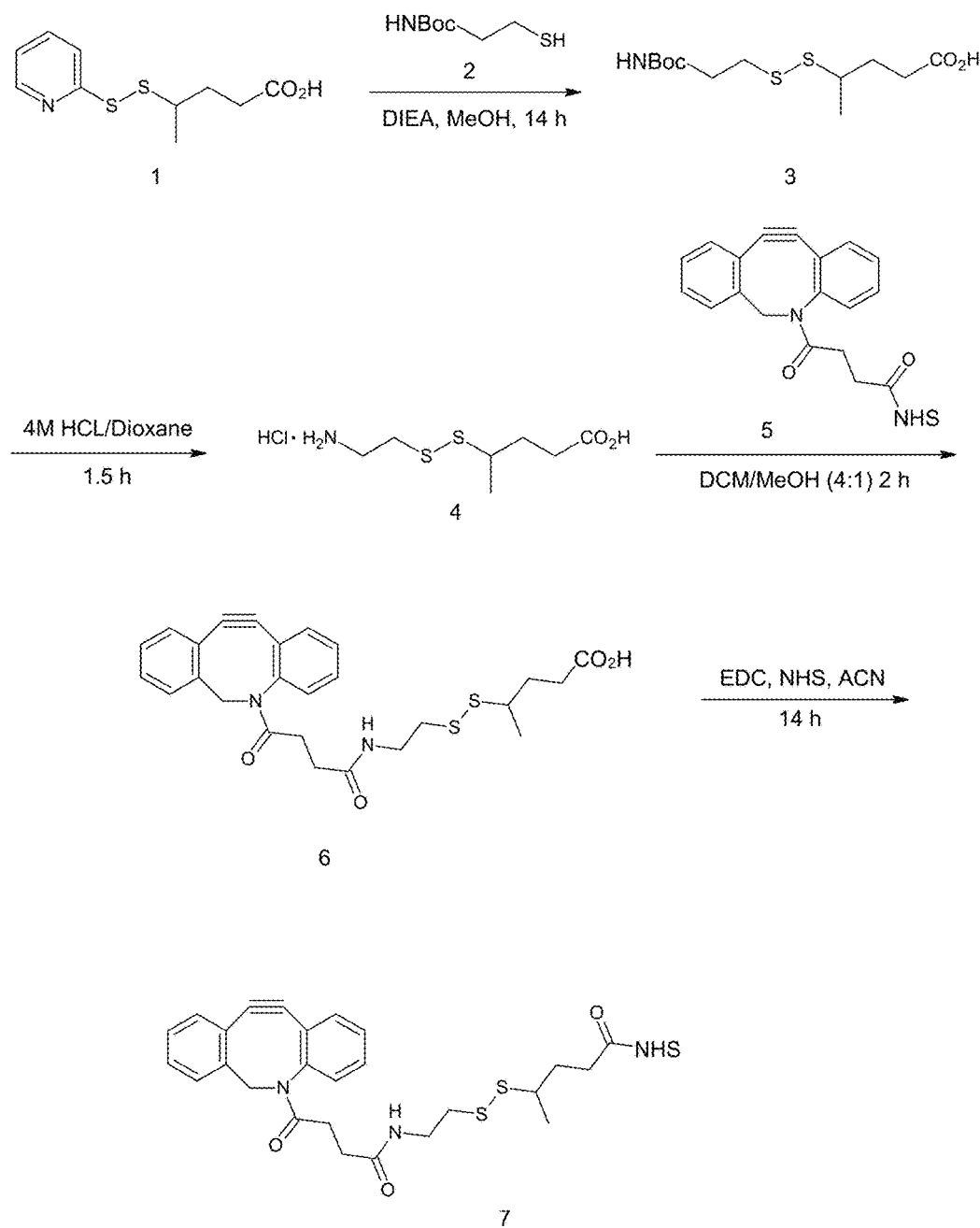
FIG. 1. Reaction scheme illustrating synthesis of DBCO-alkane-SS—NHS.

Novel compounds comprising cyclooctynes and branched disulfides, their synthesis, and methods of use thereof, are disclosed herein. The improved compounds disclosed herein exhibit improved stability with respect to previously described compositions containing cyclooctynes.

Disclosed herein are cyclooctyne-alkyl-disulfide-modified oligonucleotides, their synthesis, and methods of use thereof. The cyclooctyne-alkyl-disulfide-modified oligonucleotides are readily attached to a compound of interest such as a targeting ligand, lipid, cholesterol, delivery agent (such as an endosomolytic polymer), or pharmacological modifier. The cyclooctyne-alkyl-disulfide-modified oligonucleotides are more readily synthesized with improved yield, and have fewer impurities than corresponding cyclooctyne-disulfide-modified oligonucleotides.

In some embodiments, the cyclooctyne-alkyl disulfide compounds have the structure represented by:

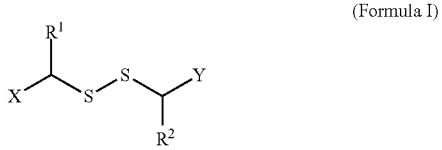

(Formula I)

wherein
$R^1$ is an alkyl group and $R^2$ is hydrogen, or $R^1$ is hydrogen and $R^2$ is an alkyl group, or $R^1$ and $R^2$ are alkyl groups.
X comprises a cyclooctyne,
Y comprises a reactive group or a synthetic oligonucleotide.
X and Y may be attached via linkers. In some embodiments, an alkyl group is methyl or ethyl. In some embodiments, the alkyl group is methyl. In some embodiments, Y comprises an RNAi agent.

In some embodiments, the cyclooctyne-alkyl disulfide compounds have the structure represented by:

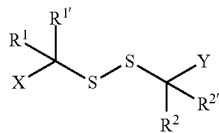

(Formula Ia)

wherein
one or more of $R^1$, $R^{1'}$, R2, and R2' alkyl groups,
X comprises a cyclooctyne,
Y comprises a reactive group or a synthetic oligonucleotide.

X and Y may be attached via linkers. In some embodiments, the alkyl groups are independently methyl or ethyl. In some embodiments, the alkyl group is methyl. In some embodiments, $R^1$ and $R^{1'}$ are alkyl groups and $R^2$ and $R^{2'}$ are hydrogens. In some embodiments, $R^2$ and $R^{2'}$ are alkyl groups and $R^1$ and $R^{1'}$ are hydrogens. In some embodiments, $R^1$, $R^{1'}$, $R^2$, and $R^{2'}$ are alkyl groups. In some embodiments, $R^1$ is an alkyl groups and $R^{1'}$, $R^2$, and $R^{2'}$ are hydrogens. In some embodiments, $R^{1'}$ are alkyl groups and $R^1$, $R^2$, and $R^{2'}$ are hydrogens. In some embodiments, $R^2$ are alkyl groups and $R^1$, $R^{1'}$, and $R^{2'}$ are hydrogens. In some embodiments, $R^{2'}$ are alkyl groups and $R^1$, $R^{1'}$, and $R^2$ are hydrogens. In some embodiments, $R^1$, $R^{1'}$, and $R^2$ are alkyl groups $R^{2'}$ is a hydrogen. In some embodiments, $R^1$, $R^{1'}$, and $R^{2'}$ are alkyl groups $R^2$ is a hydrogen. In some embodiments, $R^1$, $R^2$, and $R^2$ are alkyl groups $R^{1'}$ is a hydrogen. In some embodiments, $R^{1'}$, $R^2$, and $R^{2'}$ are alkyl groups $R^1$ is a hydrogen. In some embodiments, Y comprises an RNAi agent.

In some embodiments, the cyclooctyne-alkyl disulfide compounds have the structure represented by:

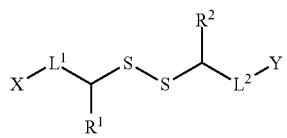

(Formula II)

wherein
$R^1$ is an alkyl group and $R^2$ is hydrogen, or $R^1$ is hydrogen and $R^2$ is an alkyl group, or $R^1$ and $R^2$ are alkyl groups,
$L^1$ and $L^2$ are linkers,
X comprises a cyclooctyne, and
Y comprises a reactive group or a synthetic oligonucleotide.

In some embodiments, the alkyl group is methyl or ethyl. In some embodiments, the alkyl group is methyl. In some embodiments, Y comprises an RNAi agent.

In some embodiments, the cyclooctyne-alkyl disulfide compounds have the structure represented by:

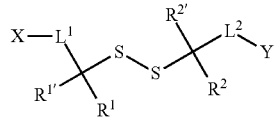

(Formula IIa)

wherein
one or more of $R^1$, $R^{1'}$ $R^2$ and $R^{2'}$ are alkyl groups,
$L^1$ is a first linker,
$L^2$ is a second linker,
X comprises a cyclooctyne, and
Y comprises a reactive group or a synthetic oligonucleotide.

In some embodiments, the alkyl groups are independently methyl or ethyl. In some embodiments, the alkyl group is methyl. In some embodiments, $R^1$ and $R^{1'}$ are alkyl groups and $R^2$ and $R^{2'}$ are hydrogens. In some embodiments, $R^2$ and $R^{2'}$ are alkyl groups and $R^1$ and $R^{1'}$ are hydrogens. In some embodiments, $R^1$, $R^{1'}$, $R^2$, and $R^{2'}$ are alkyl groups. In some embodiments, $R^1$ is an alkyl groups and $R^{1'}$, $R^2$, and $R^{2'}$ are hydrogens. In some embodiments, $R^{1'}$ are alkyl groups and $R^1$, $R^2$, and $R^{2'}$ are hydrogens. In some embodiments, $R^2$ are alkyl groups and $R^1$, $R^{1'}$, and $R^{2'}$ are hydrogens. In some embodiments, $R^{2'}$ are alkyl groups and $R^1$, $R^{1'}$, and $R^2$ are hydrogens. In some embodiments, $R^1$, $R^{1'}$, and $R^2$ are alkyl groups $R^{2'}$ is a hydrogen. In some embodiments, $R^1$, $R^{1'}$, and $R^{2'}$ are alkyl groups $R^2$ is a hydrogen. In some embodiments, $R^1$, $R^2$, and $R^2$ are alkyl groups $R^{1'}$ is a hydrogen. In some embodiments, $R^{1'}$, $R^2$, and $R^{2'}$ are alkyl groups $R^1$ is a hydrogen. In some embodiments, Y comprises an RNAi agent.

In some embodiments, the cyclooctyne-alkyl disulfide compounds have the structure represented by:

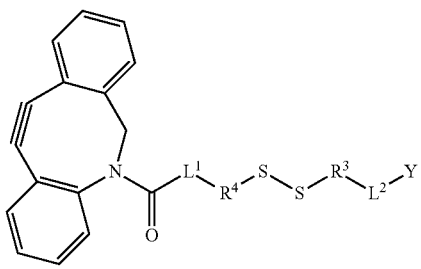

(Formula III)

wherein
$R^3$ is $C(R^5R^6)$ wherein $R^5$ is hydrogen, methyl or ethyl, and $R^6$ is hydrogen, methyl or ethyl,
$R^4$ is $C(R^7R^8)$ wherein $R^7$ is hydrogen, methyl or ethyl, and $R^8$ is hydrogen, methyl or ethyl,
at least one of $R^5$, $R^6$, $R^7$, and $R^8$ is methyl or ethyl,
$L^1$ is a first linker,
$L^2$ is a second linker, and
Y comprises a reactive group or a synthetic oligonucleotide.

In some embodiments, $R^5$ or $R^6$ is methyl or ethyl, and $R^7$ and $R^8$ are both hydrogen. In some embodiments, $R^5$ is methyl or ethyl, and $R^6$, $R^7$ and $R^8$ are hydrogen. In some embodiments, $R^6$ is methyl or ethyl, and $R^5$, $R^7$ and $R^8$ are hydrogen. In some embodiments, $R^5$ and $R^6$ are independently methyl or ethyl, and $R^7$ and $R^8$ are both hydrogen. In some embodiments, $R^7$ or $R^8$ is methyl or ethyl, and $R^5$ and $R^6$ are both hydrogen. In some embodiments, $R^7$ is methyl or ethyl, and $R^8$, $R^5$ and $R^6$ are hydrogen. In some embodiments, $R^8$ is methyl or ethyl, and $R^7$, $R^5$ and $R^6$ are hydrogen. In some embodiments, $R^7$ and $R^8$ are independently methyl or ethyl, and $R^5$ and $R^6$ are both hydrogen. In some embodiments, $R^5$ is $CH_3$, and $R^6$, $R^7$ and $R^8$ are each hydrogen. In some embodiments, $R^7$ is $CH_3$, and $R^5$, $R^6$ and R[8] are each hydrogen. In some embodiments, the synthetic oligonucleotide is an RNAi agent.

In some embodiments, the cyclooctyne-alkyl disulfide compounds have the structure represented by:

(Formula IIIa)

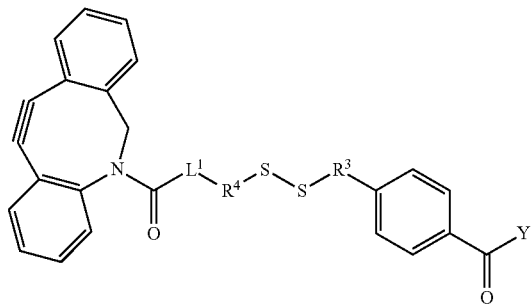

wherein
- R[3] is C(R[5]R[6]) wherein R[5] is hydrogen, methyl or ethyl, and R[6] is hydrogen, methyl or ethyl,
- R[4] is C(R[7]R[8]) wherein R[7] is hydrogen, methyl or ethyl, and R[8] is hydrogen, methyl or ethyl,
- at least one of R[5], R[6], R[7], and R[8] is methyl or ethyl,
- L[1] is a linker, and
- Y comprises a reactive group or a synthetic oligonucleotide.

In some embodiments, R[5] or R[6] is methyl or ethyl, and R[7] and R[8] are both hydrogen. In some embodiments, R[5] is methyl or ethyl, and R[6], R[7] and R[8] are hydrogen. In some embodiments, R[6] is methyl or ethyl, and R[5], R[7] and R[8] are hydrogen. In some embodiments, R[5] and R[6] are independently methyl or ethyl, and R[7] and R[8] are both hydrogen. In some embodiments, R[7] or R[8] is methyl or ethyl, and R[5] and R[6] are both hydrogen. In some embodiments, R[7] is methyl or ethyl, and R[8], R[5] and R[6] are hydrogen. In some embodiments, R[8] is methyl or ethyl, and R[7], R[5] and R[6] are hydrogen. In some embodiments, R[7] and R[8] are independently methyl or ethyl, and R[5] and R[6] are both hydrogen. In some embodiments, R[5] is CH$_3$, and R[6], R[7] and R[8] are each hydrogen. In some embodiments, R[7] is CH$_3$, and R[5], R[6] and R[8] are each hydrogen. In some embodiments, the synthetic oligonucleotide is an RNAi agent.

In some embodiments, the cyclooctyne-alkyl-disulfide-amine reactive group compounds have the structure represented by:

(Formula IV)

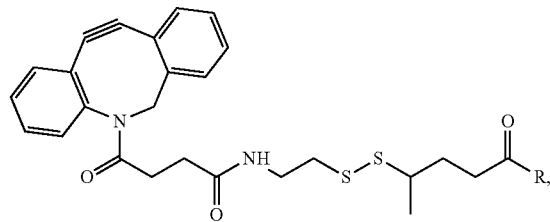

(Formula V)

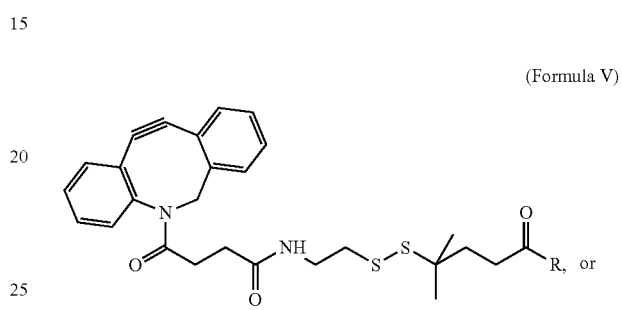

(Formula VI)

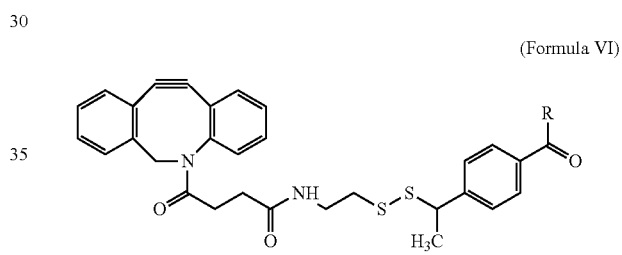

wherein R comprises a reactive group selected from the group comprising: activated ester, NHS, TFP, PFP, tetrazine, norbornenes, trans-cyclooctenes, hydrazines (e.g. hynic), aminooxy reagents, and aldehydes (e.g. 4-formyl benzoic acid).

Figure 5:
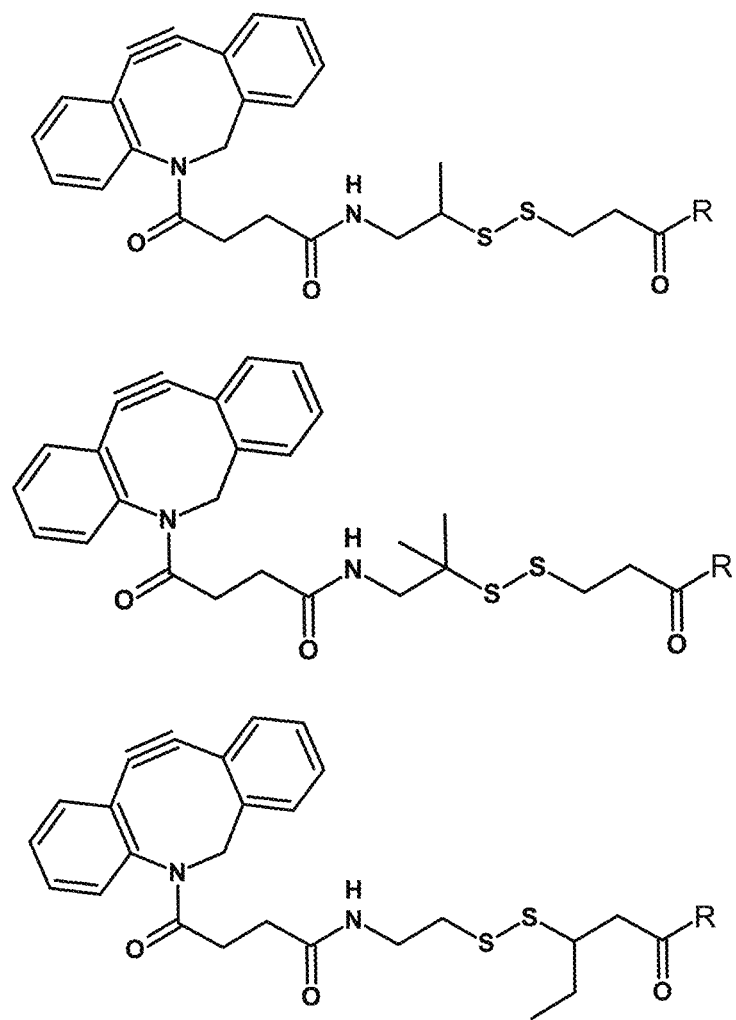
FIG. 5. Disclosed embodiments of certain cyclooctyne-alkyl-S—S compounds. R comprises a reactive group, NHS reaction group, synthetic oligonucleotide, or RNAi agent. n and m are integers from 0 to 10.
Figure 6:
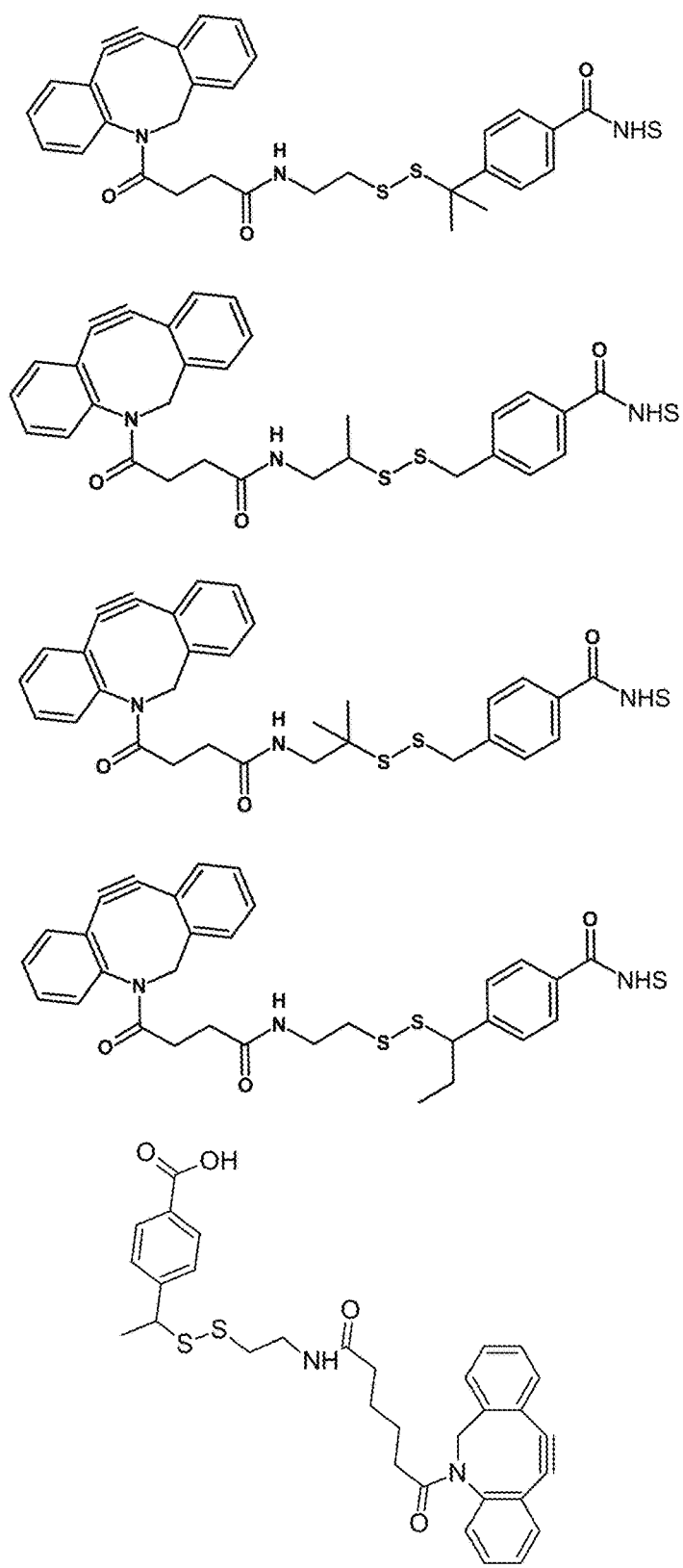
FIG. 6. Disclosed embodiments of certain cyclooctyne-alkyl-S—S compounds. R comprises a reactive group, NHS reaction group, synthetic oligonucleotide, or RNAi agent.

In some embodiments, the cyclooctyne-alkyl-S—S-amine reactive group compounds have the structures shown in FIGS. 5-6.

In some embodiments, the cyclooctyne-alkyl-S—S-synthetic oligonucleotide compounds have the structures represented by:

(Formula VII)

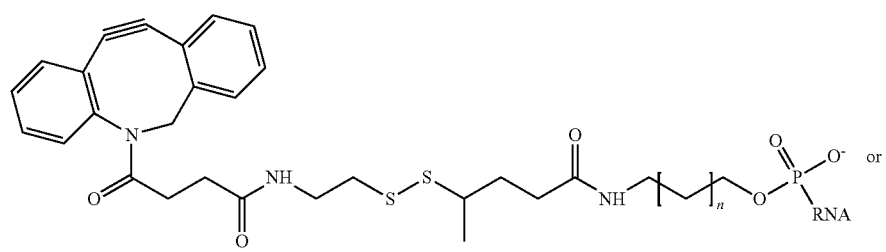

(Formula VIII)

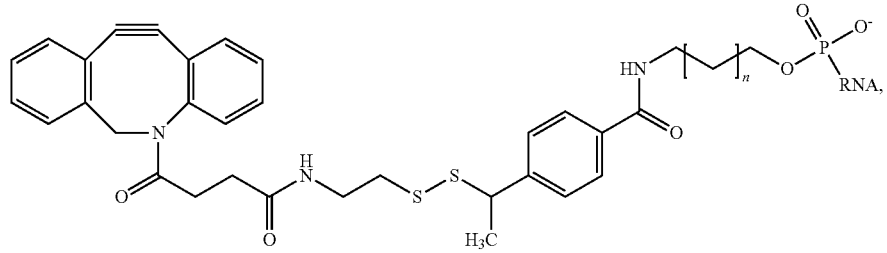

wherein RNA comprises an RNAi agent.

In some embodiments, the described cyclooctyne-alkyl-S—S-synthetic oligonucleotide compounds are used to link the oligonucleotide to an azide-containing compound. In some embodiments, the azide-containing compound is selected from the group comprising: targeting ligand, lipid, cholesterol, or delivery agent, such as an endosomolytic polymer, polyamine, modified polyamine, or pharmacological modifier.

In some embodiments, the described cyclooctyne-alkyl-S—S-oligonucleotide is conjugated to a polymer, wherein said polymer contains an azide group. In some embodiments, the polymer is a polymer that facilitates in vivo delivery of the oligonucleotide. In some embodiments, the oligonucleotide comprises an RNAi agent.

Disclosed herein are methods of covalently linking a synthetic oligonucleotide, such as an RNAi agent, to a pharmaceutical modifier or delivery polymer wherein the synthetic oligonucleotide is conjugated to a described cyclooctyne-alkyl-disulfide-amine reactive group compound to form a cyclooctyne-alkyl-S—S-synthetic oligonucleotide. In some embodiments, the cyclooctyne-alkyl-S—S-synthetic oligonucleotide is further reacted with a pharmaceutical modifier or delivery polymer, wherein said pharmaceutical modifier or delivery polymer comprises at least one azide group.

The described compounds and methods can be used to form RNAi agent-containing compositions that are used as therapeutic agents, as diagnostic agents, or for use in molecular biology research.

As used herein, a cyclooctyne is a copper-free alkyne conjugation reagent. Cyclooctynes include, but are not limited to: diarylcyclooctyne, DBCO (also Azadibenzocyclooctyne (DIBAC or ADIBO)), a cyclooctyne moiety fused to aryl groups (benzoannulated systems),

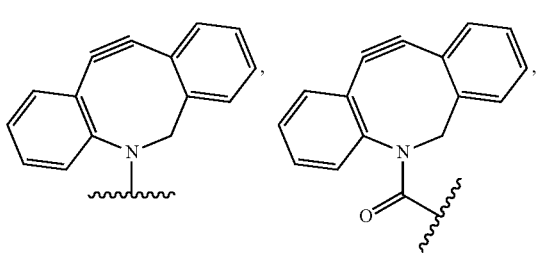

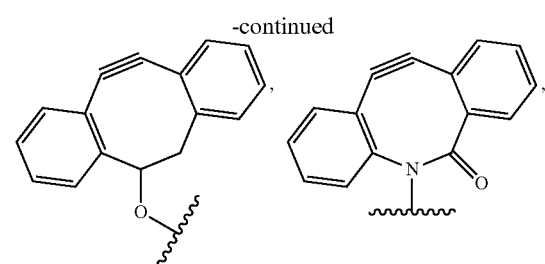

wherein X=C or N,

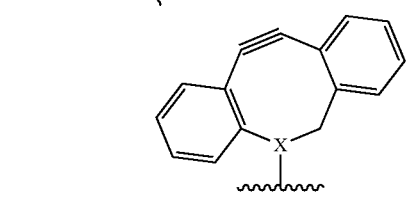

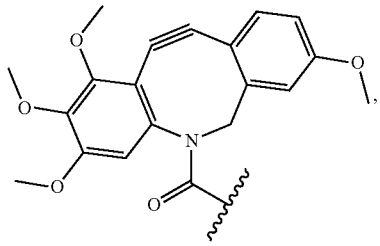

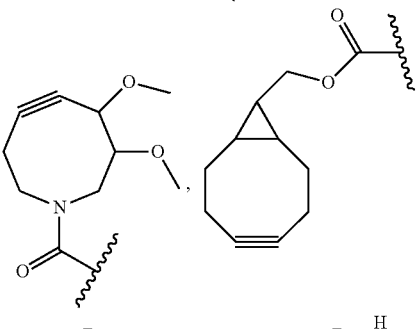

, and

As used herein, the term "linker" means an organic moiety that connects two parts of a compound. Linkers typically comprise a direct bond or an atom such as oxygen or sulfur, a unit such as $NR^L$ (where $R^L$ is hydrogen, acyl, aliphatic or substituted aliphatic), C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^L)$ (where $R^L$ is hydrogen, acyl, aliphatic or substituted aliphatic), C(O), substituted or unsubstituted aryl, substituted or unsubstituted heteroaryl, substituted or unsubstituted heterocyclic; $-(CH_2)_n-$, $-(CH_2)_nN-$, $-(CH_2)_nO-$, $-(CH_2)_nS-$, $-(CH_2)_n-C(O)-$, $-C(O)-(CH_2)_n-C(O)-NH-(CH_2)_m-C(O)-NH-(CH_2)_x-$, $-C(O)-(CH_2)_n-C(O)-NH-(CH_2)_m-C(O)-(CH_2)_n-C(O)-(CH_2)_m-$, $-C(O)-(CH_2)_n-NH-C(O)-(CH_2)_m-$, $-C(O)-(CH_2)_n-O-(CH_2-CH_2-O)_m-(CH_2)_x-$, $-(O-CH_2-CH_2)_n-$, $-O-(CH_2-CH_2-O)_n-$, $-O-(CH_2-CH_2-O)_n-CH_2-$, $-CH_2-(O-CH_2-CH_2)_n-$, $-CH_2-(O-CH_2-CH_2)_n-O-$, $-CH_2-(O-CH_2-CH_2)_n-O-CH_2-$, $-CH_2-CH_2-(O-CH_2-CH_2)_n-$, $-(CH_2-CH_2-O)_n-$, $-(CH_2-CH_2-O)_n-CH_2-$,

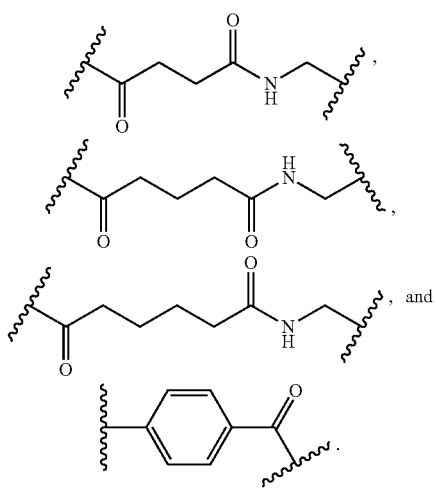

Reactive groups are those commonly available in the art and include, but are not limited to, activated ester, NHS, TFP, PFP, tetrazine, norbornenes, trans-cyclooctenes, hydrazines (e.g. hynic), aminooxy reagents, and aldehydes (e.g. 4-formyl benzoic acid).

Targeting ligands (also referred to as targeting groups) are used for targeting or delivery of a compound to target cells or tissues, or specific cell types. Targeting ligands enhance the association of molecules to a target cell. Thus, targeting ligands can enhance the pharmacokinetic or biodistribution properties of a conjugate to which they are attached to improve cellular distribution and cellular uptake of the conjugate. Binding of a targeting group to a cell or cell receptor may initiate endocytosis. Targeting groups may be monovalent, divalent, trivalent, tetravalent, or have higher valency. Targeting groups can be, but are not limited to, compounds with affinity to cell surface molecules, cell receptor ligands, antibodies, monoclonal antibodies, antibody fragments, and antibody mimics with affinity to cell surface molecules, hydrophobic groups, cholesterol, cholesteryl groups, or steroids. In some embodiments, a targeting group comprises a cell receptor ligand. A variety of targeting groups have been used to target drugs and genes to cells and to specific cellular receptors. Cell receptor ligands may be, but are not limited to: carbohydrates, glycans, saccharides (including, but not limited to: galactose, galactose derivatives (such as N-acetyl-galactosamine), mannose, and mannose derivatives), haptens, vitamins, folate, biotin, aptamers, and peptides (including, but not limited to: RGD-containing peptides, RGD mimics, insulin, EGF, and transferrin).

As used herein, a steric stabilizer is a non-ionic hydrophilic polymer (either natural, synthetic, or non-natural) that prevents or inhibits intramolecular or intermolecular interactions of a molecule to which it is attached relative to the molecule containing no steric stabilizer. A steric stabilizer hinders a molecule to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a molecule. A preferred steric stabilizer is a polyethylene glycol (PEG) or PEG derivative. PEG molecules suitable for the invention have about 1-120 ethylene glycol monomers.

As used herein, a "pharmaceutical composition" comprises a pharmacologically effective amount of at least one kind of RNAi agent and one or more a pharmaceutically acceptable excipients. Pharmaceutically acceptable excipients (excipients) are substances other than the Active Pharmaceutical ingredient (API, therapeutic product, e.g., RNAi agent) that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use.

Excipients include, but are not limited to: absorption enhancers, anti-adherents, anti-foaming agents, anti-oxidants, binders, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents. A pharmaceutically acceptable excipient may or may not be an inert substance.

The pharmaceutical compositions can contain other additional components commonly found in pharmaceutical compositions. The pharmaceutically-active materials may include, but are not limited to: anti-pruritics, astringents, local anesthetics, or anti-inflammatory agents (e.g., antihistamine, diphenhydramine, etc.). It is also envisaged that cells, tissues or isolated organs that express or comprise the herein defined RNAi agents may be used as "pharmaceutical compositions". As used herein, "pharmacologically effective amount," "therapeutically effective amount," or simply "effective amount" refers to that amount of an RNAi agent to produce the intended pharmacological, therapeutic or preventive result.

As used herein, a pharmacological modifier is a compound that protects, supports, or enhances stability, bioavailability, delivery, effectiveness, or patient acceptability of an API during storage or use.

As used herein a delivery polymer is a polymer that enhances in vivo bioavailability or delivery of an API. Examples of delivery polymers include, but are not limited to: amphipathic membrane active polyamines, and reversibly modified amphipathic membrane active polyamines.

As used herein, membrane active polyamines are surface active, amphipathic polyamines that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polyamine's activity in at least one the following assays: red blood cell lysis (hemolysis), liposome leakage, liposome fusion, cell fusion, cell lysis, and endosomal release. Polyamines that preferentially cause disruption of endosomes or lysosomes over plasma membranes are considered endosomolytic. The effect of membrane active polyamines on a cell membrane may be transient. Membrane active polyamines possess affinity for the membrane and cause a denaturation or deformation of bilayer structures. Delivery of an RNAi agent to a cell is mediated by the membrane active polyamine disrupting or destabilizing the plasma membrane or an internal vesicle membrane (such as an endosome or lysosome), including by forming a pore in the membrane, or disrupting endosomal or lysosomal vesicles thereby permitting release of the contents of the vesicle into the cell cytoplasm. In some embodiments, the membrane active polyamine comprises melittin or a melittin-like peptide (MLP).

The term polynucleotide, or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Synthetic oligonucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

The synthetic oligonucleotides of the invention can be chemically modified. The use of chemically modified polynucleotides can improve various properties of the polynucleotide including, but not limited to: resistance to nuclease degradation in vivo, cellular uptake, activity, and sequence-specific hybridization. Non-limiting examples of such chemical modifications include: phosphorothioate internucleotide linkages, 2'-O-methyl ribonucleotides, 2'-deoxy-2'-fluoro ribonucleotides, 2'-deoxyribonucleotides, "universal base" nucleotides, 5-C-methyl nucleotides, 2',3'-seco nucleotide mimics (unlocked nucleobase analogues, represented herein as $N_{UNA}$ or NUNA), and inverted deoxyabasic residue incorporation. These chemical modifications, when used in various polynucleotide constructs, are shown to preserve polynucleotide activity in cells while at the same time, dramatically increasing the serum stability of these compounds.

In some embodiments, a synthetic oligonucleotide of the invention comprises a duplex having two strands, one or both of which can be chemically-modified, wherein each strand is about 19 to about 29 (e.g., about 19, 20, 21, 22, 23, 24, 25, 26, 27, 28,or 29) nucleotides. In some embodiments, a synthetic oligonucleotide of the invention comprises one or more modified nucleotides. A synthetic oligonucleotide of the invention can comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions).

A synthetic oligonucleotide may comprise a 5' or 3' end modification. 3' and 5' end modifications include, but are not limited to: amine-containing groups, alkyl groups, alkyl amine groups, reactive groups, TEG groups, and PEG groups.

An "RNAi agent" (also called an "RNAi trigger", or a double stranded RNA interference polynucleotide) inhibits gene expression through the biological process of RNA interference (RNAi). RNAi agents comprise double stranded RNA or RNA-like structures typically containing 15-50 base pairs, and preferably 18-26 base pairs, and have a nucleobase sequence at least 85% complementary to a coding sequence in an expressed target gene within the cell. RNAi agents include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599 8,349,809 and 8,513,207). As used herein, the terms RNAi agent and RNAi trigger are used interchangeably.

By inhibit, down-regulate, or knockdown gene expression, it is meant that the expression of the gene, as measured by the level of mRNA transcribed from the gene or the level of polypeptide, protein or protein subunit translated from the mRNA, is reduced below that observed in the absence of the compounds disclosed herein. Inhibition, down-regulation, or knockdown of gene expression, with a polynucleotide delivered by the compositions of the invention, is preferably below that level observed in the presence of a control inactive polynucleotide, a polynucleotide with a scrambled sequence or with inactivating mismatches, or in the absence of conjugation of the polynucleotide to the compositions disclosed herein.

In some embodiments, the RNAi agent comprises at least two sequences that are partially, substantially, or fully complementary to each other. In some embodiments, the two RNAi agent sequences comprise a sense strand comprising a first sequence and an antisense strand comprising a second sequence. In some embodiments, the two RNAi agent sequences comprise two sense strands which together comprise a first sequence and an antisense strand comprising a second sequence, wherein the sense strands and the antisense strand together form a meroduplex. The sense strand may be connected to the antisense strand via a linking molecule, such as a polynucleotide linker or a non-nucleotide linker.

The antisense strand comprises a nucleotide sequence which is complementary to a part of an mRNA encoded by a target gene, and the region of complementarity is most preferably less than 30 nucleotides in length. The RNAi agent sense strands comprise sequences which have an identity of at least 85% to at least a portion of a target mRNA. The RNAi agent, upon delivery to a cell expressing the target gene, inhibits the expression of said target gene in vitro or in vivo.

In some embodiments, the RNAi agent may be comprised of naturally occurring nucleotides or may be comprised of at least one modified nucleotide or nucleotide mimic. The RNAi agent sense and antisense strands of the invention may be synthesized and/or modified by methods well established in the art. RNAi agent nucleosides, or nucleotide bases, may be linked by phosphate-containing (natural) or non-phosphate-containing (non-natural) covalent internucleoside linkages, i.e. the RNAi agent may have natural or non-natural oligonucleotide backbones. In some embodiments, the RNAi agent contains a non-standard (non-phosphate) linkage between to nucleotide bases.

As used herein, a "modified nucleotide" is a nucleotide, nucleotide mimic, abasic site, or a surrogate replacement moiety other than a ribonucleotide (2'-hydroxyl nucleotide). In one embodiment a modified nucleotide comprises a 2'-modified nucleotide (i.e. a nucleotide with a group other than a hydroxyl group at the 2' position of the five-membered sugar ring). Modified nucleotides include, but are not limited to: 2'-modified nucleotides, 2'-O-methyl nucleotides, 2'-deoxy-2'-fluoro nucleotides, 2'-deoxy nucleotides, 2'-methoxyethyl (2'-O-2-methoxylethyl) nucleotides, 2'-amino nucleotides, 2'-alkyl nucleotides, 3' to 3' linkages (inverted) nucleotides, non-natural base comprising nucleotides, bridged nucleotides, peptide nucleic acids, 2',3'-seco nucleotide mimics (unlocked nucleobase analogues, locked nucleotides, 3'-O-Methoxy (2' internucleotide linked) nucleotide, 2'-F-Arabino nucleotides, morpholino nucleotides, vinyl phosphonate deoxyribonucleotides, vinyl phosphonate nucleotides, and abasic nucleotides. It is not necessary for all positions in a given RNAi agent be uniformly modified. Conversely, more than one modification may be incorporated in a single RNAi agent or even in a single nucleotide thereof. The RNAi agent sense strands and antisense strands described herein may be synthesized and/or modified by methods known in the art. Modification at each nucleotide is independent of modification of the other nucleotides.

In some embodiments, an RNAi agent may comprise a 5' or 3' end modification. 3' and 5' end modifications include, but are not limited to: amine-containing groups, alkyl groups, alkyl amine groups, reactive groups, TEG groups, and PEG groups.

In some embodiments, the RNAi agent may comprise overhangs, i.e. typically unpaired, overhanging nucleotides which are not directly involved in the double helical structure normally formed by the core sequences of the herein defined pair of sense strand and antisense strand.

In some embodiments, the RNAi agent may contain 3' and/or 5' overhangs of 1-5 bases independently on each of the sense strands and antisense strands. In some embodiments, both the sense strand and the antisense strand contain 3' and 5' overhangs. In some embodiments, one or more of the 3' overhang nucleotides of one strand base pairs with one or more 5' overhang nucleotides of the other strand. In some embodiments, the one or more of the 3' overhang nucleotides of one strand do not pair with the one or more 5' overhang nucleotides of the other strand. The sense and antisense strands of an. RNAi agent may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In some embodiments, one or more of the nucleotides in the overhang contains a thiophosphate, phosphorothioate, deoxynucleotide inverted (3' to 3' linked) nucleotide, or is a modified ribonucleotide or deoxynucleotide.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi agent molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

EXAMPLES

Example 1

Synthesis of DBCO—S—S-methyl-NHS (FIG. 1, Compound 7)

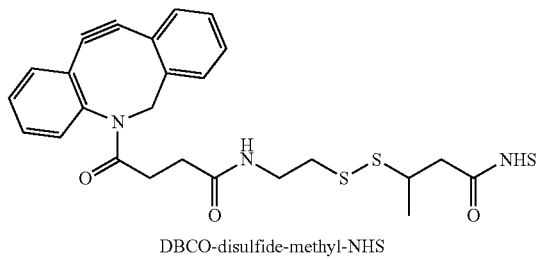

DBCO-disulfide-methyl-NHS

A) N-Boc-Aminoacid 3: 4-(Pyridin-2-yldisulfanyl)pentanoic acid 1 (Annova Chem., INC., product #L10067, 800 mg, 3.29 mmol) was stirred for 14 h with 2-(boc-amino) ethanethiol 2 (1.748 g, 9.86 mmol) and DIEA (1.72 mL, 9.86 mmol) in anhydrous MeOH (15 mL) under Ar at RT. The solvent was removed on a rotavapor, the residue was redissolved in DCM (100 mL), washed with 5% KHSO₄ (2×20 mL), H₂O (1×25 mL), and brine (1×20 mL). The crude product was dried over Na₂SO₄, filtered and concentrated on a rotavapor. Column purification on a SiO₂ (eluent gradient hexane:EtOAc:acetic acid=9:1: 0.05-7:3:0.05) yielded 650 mg (70%) of a pure product 3.

B) Aminoacid 4: The product 3 (650 mg, 2.28 mmol) was stirred for 10 min in an ice-cold solution of HCl/Dioxane (4M, 6 mL) and for 1.5 h at RT. All volatiles were removed on a rotavapor, the residue was taken in DMF (2.5 mL) and crushed in Et₂O (40 mL). The separated product was triturated with Et₂O and dried in vacuo. Yield 416 mg.

C) Compound DBCO NHS 5 was prepared in 8 steps following literature procedures.

D) DBCO derivative 6: The amino acid 4 (410 mg, 2.22 mmol) was stirred for 2 h with dibenzocyclooctyne-N-hydroxysuccinimidyl (Sigma-Aldrich) (893 mg, 2.22 mmol) and DIEA (0.965 mL, 5.54 mmol) in DCM/MeOH solution (4:1, 20 mL). All volatiles were removed on a rotavap, the residual DIEA was removed by two successive evaporations of dioxane from the crude. The product was purified on a SiO₂ column (eluent: gradient 2%-4% MeOH in CHCl₃. Yield 706 mg (68%).

E) DBCO-(monomethyl)Alkyne-S—S—NHS 7: The product 6 (700 mg, 1.48 mmol) was dissolved in anhydrous ACN (25 mL) and cooled on an ice bath. NHS (196 mg, 1.706 mmol) and EDC (326 mg, 1.706 mmol) were added and stirred for 30 min. The ice bath was replaced and stirring was continued for 14 h at RT. All volatiles were removed in vacuo, the residue was redissolved in CHCl₃ (125 mL), washed with 2% KHSO₄ (2×25 mL), brine (2×25 mL), dried (Na₂SO₄) filtered and concentrated in vacuo. Yield 802 mg (95%). (NMR: AB)

F) DBCO-dimethyl-S—S—NHS

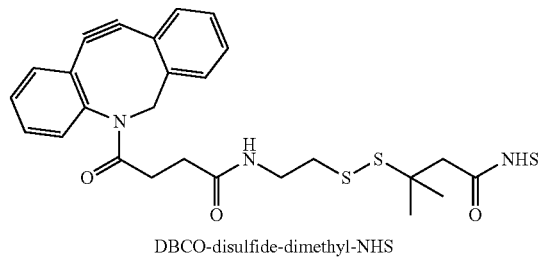

DBCO-disulfide-dimethyl-NHS

DBCO-disulfide-dimethyl-NHS was prepared similarly to 7 using:

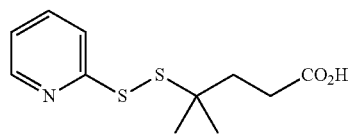 [SMILES: CC(C)(CCC(=O)O)SSc1ccccn1]

as a starting material.

G) Related compounds are readily made using similar techniques, including, but not limited to:

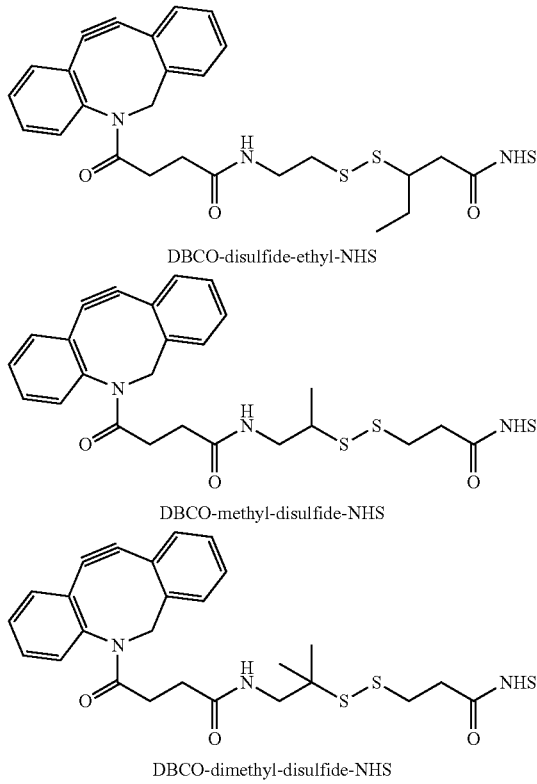

DBCO-disulfide-ethyl-NHS

DBCO-methyl-disulfide-NHS

DBCO-dimethyl-disulfide-NHS

Example 2

Figure 2:
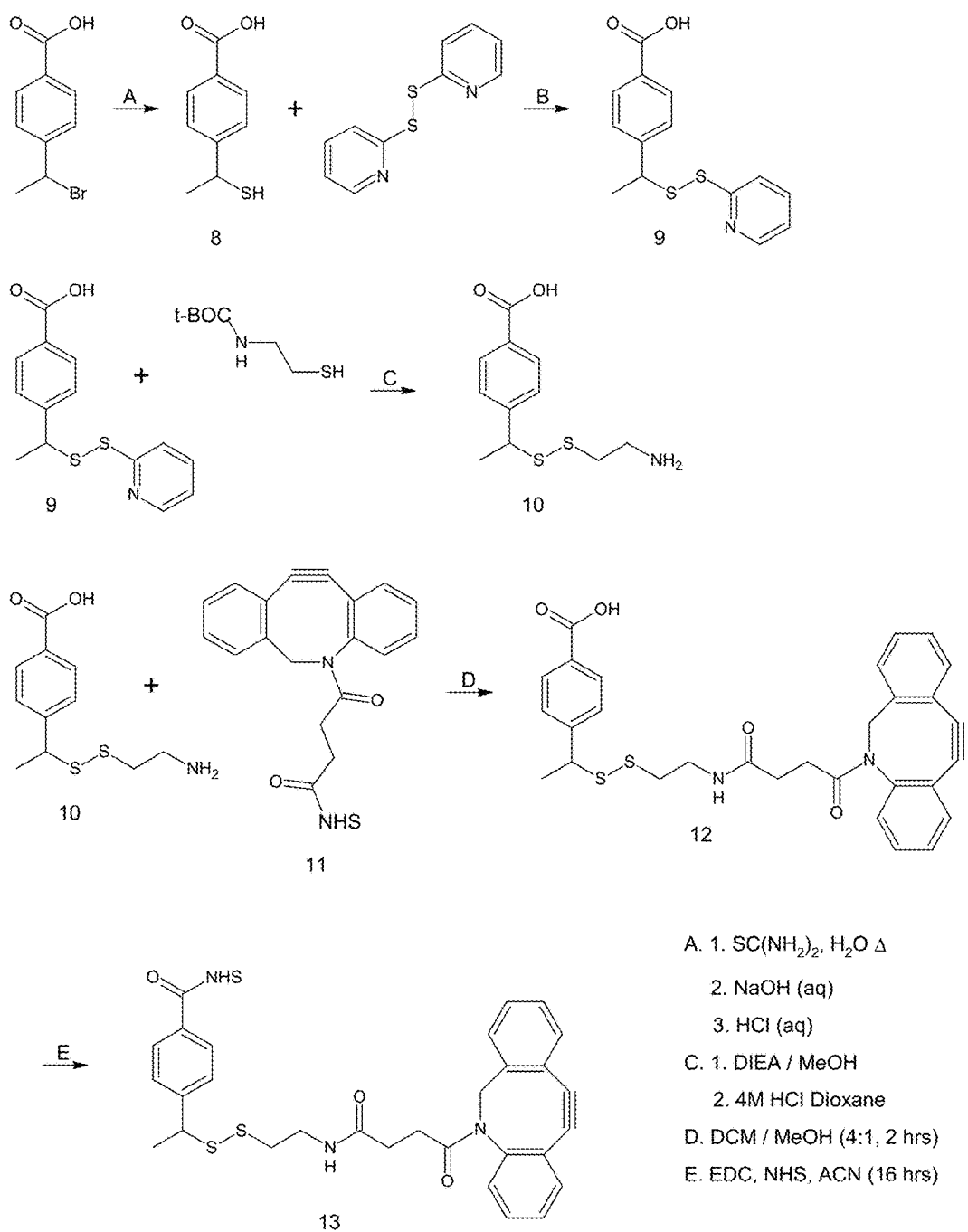
FIG. 2. Reaction scheme illustrating synthesis of DBCO-methyl-SMPT-NHS.
Figure 3:
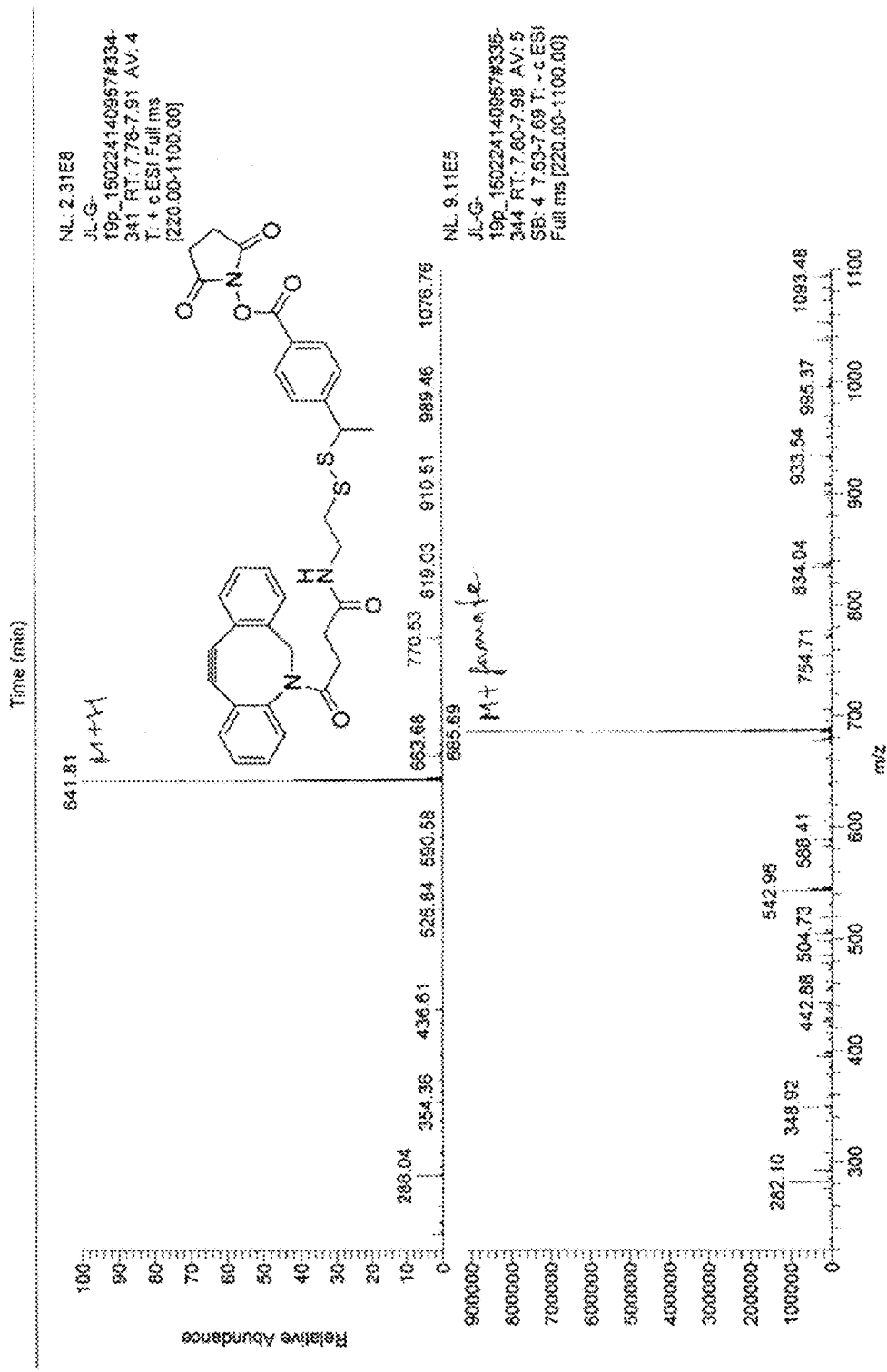
FIG. 3. Graphs showing ESI Mass Spec analysis of DBCO-methyl-SMPT-NHS.
Figure 4:
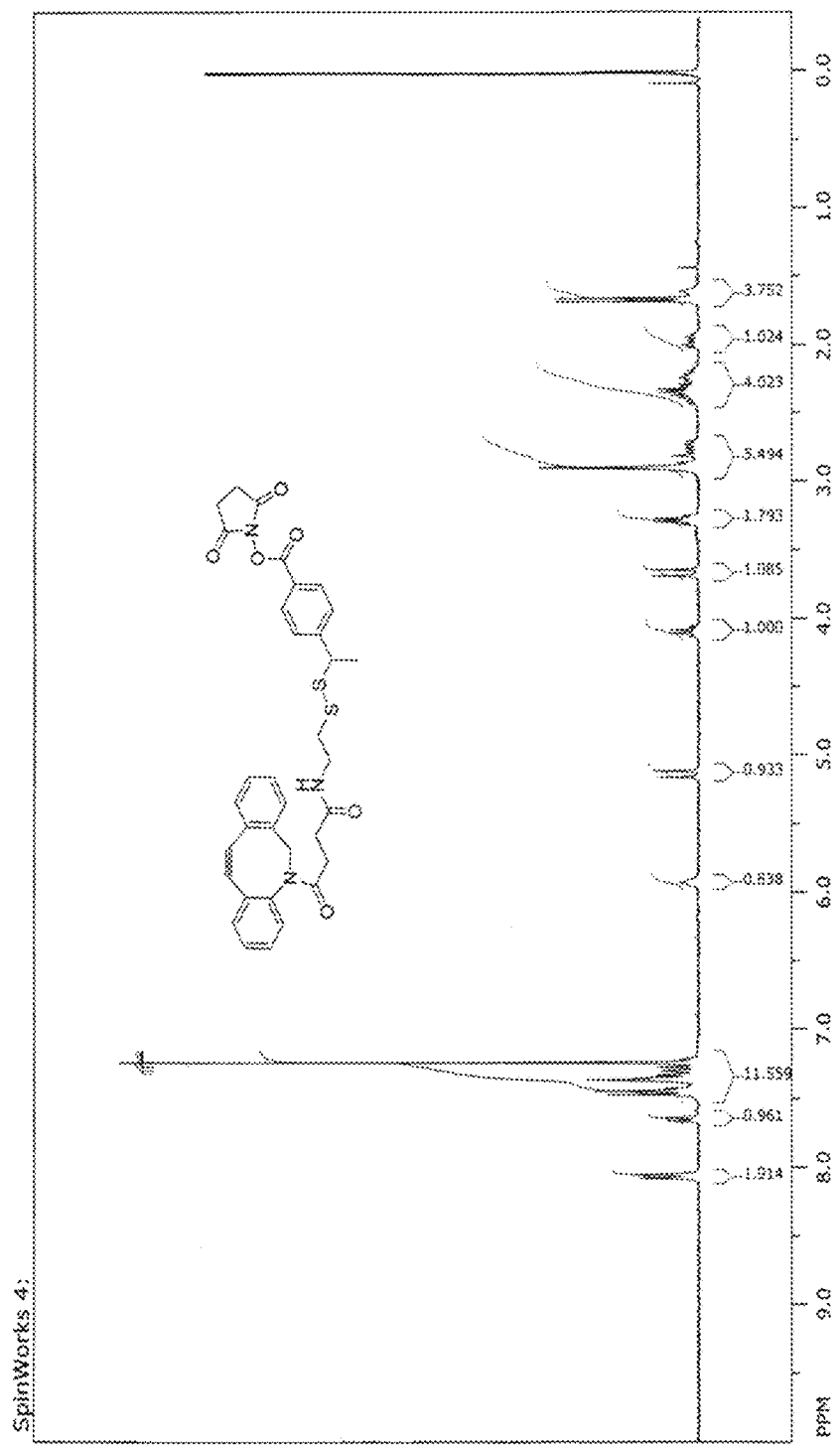
FIG. 4. Graph showing H1 NMR of DBCO-methyl-SMPT-NHS.

Synthesis of DBCO-Alkyl-SMPT-NHS (Formula VI, FIG. 2 Compound 13)

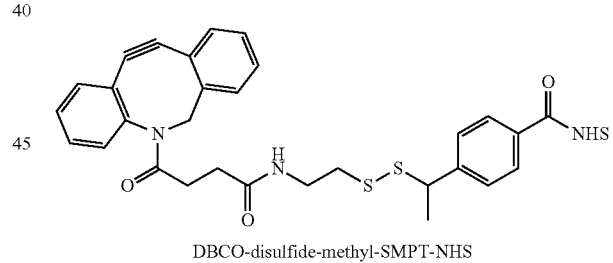

DBCO-disulfide-methyl-SMPT-NHS

A) 4-bromoethylbenzoic acid (22.7 g, 0.1 mole) and thiourea (9.3 g, 0.12 mol, 1.2 equiv.) were dissolved in H₂O (200 mL) and heated at reflux for 4 h and then 11 h at RT. 10% NaOH (aq) (120 mL) was added and heated at reflux for 3 h. Next, the mixture was chilled to room temperature, 6 M hydrochloric acid (60 mL) was added with the formation of the precipitate. The precipitate was filtered, washed with cold H₂O and dried under reduced pressure. 10.4 g (58%) of crude product 8 was used for next step.

B) A solution of 4-mercaptoethylbenzoic acid 8 (9.60 g, 52.8 mmol) in MeOH (240 mL) was added to DPDS (23.2 g, 105.6 mmol, 2 equiv.) and AcOH (3 mL, 52.8 mmol, 1 equiv dissolved in MeOH (240 mL) over 3 h while stirring in an ice bath. Afterwards, the reaction was brought to RT and continued for 2 h. Solvent was removed under reduced pressure and the remaining oil was loaded on a silica gel column. Byproducts were washed with EtOAc:EtOH:Et3N (200:10:2) and the product 9 (9.8 g, 64%) was eluted with EtOAc:EtOH:AcOH (200:20:1).

C) To a solution of acid 9 (9.7 g, 33.8 mmol) in MeOH (20 mL) was added 2-(Boc-amino)ethanethiol (6 g, 33.8 mmol) and DIEA (5.9 mL, 33.8 mmol). The mixture was stirred under Argon for 24 h at reflux. The progress of the reaction was monitored by TLC. The reaction mixture was cooled to RT, concentrated and re-dissolved in EtOAc (100 mL) and washed with saturated NaHCO$_3$ (3×30 mL) and brine. The EtOAc layer was dried over Na$_2$SO$_4$, concentrated and dried in vacuo to isolate crude product and further purified by silica gel column to give product 2A, weight 11 g, yield 91.2%. Compound 2A (11 g, 30.8 mmol) was dissolved at 0° C. in 4M HCl in dioxane (50 mL), the cooling bath was removed and the reaction was stirred at RT for 2 h. After 2 h TLC (CHCl$_3$:MeOH:AcOH (9.6:0.4:0.025)) showed no starting material present. All volatiles were removed on a rotavap at 35° C., and then triturated with Et$_2$O (2×50 mL). The product 10 (as HCl salt) was dried overnight in vacuo, weight 9.1 g, yield 100%.

D) Compound DBCO NHS 11 was prepared in 8 steps following literature procedures.

E) DBCO NHS 11 (12.4 g, 30.8 mmol) and amine 10 (9.1 g, 30.8 mmol) were dissolved in DCM/MeOH mixture (4:1, 200 mL). DIEA (11 mL, 61.6 mmol) was added and the reaction mixture was stirred for 2 h under Ar. All volatiles were removed on a rotavap, the residue was dried on an oil pump and product was purified on SiO$_2$ column (eluent: gradient 1-3% MeOH in CHCl$_3$) to give compound 12 as a white solid, weight 11.7 g, Yield 70%.

F) DBCO SMPT 13 (final product): An acid 12 (10.9 g, 20 mmol) was dissolved in ACN/THF mixture (4:1, 150 mL) and the solution was cooled on ice bath. NHS (2.3 g, 20 mmol) and EDC (4 g, 21 mmol) were successively added to the stirring reaction mixture, the cooling bath was removed and the reaction was continued for 16 h at RT. All volatiles were removed on a rotavap, the residue was redissolved in CHCl$_3$ (200 mL) and washed twice with H$_2$O (2×50 mL) and brine (50 mL). The organic phase was dried on MgSO$_4$, filtered and concentrated by a rotavap to give final product DBCO SMPT(13) as white solid, weight 12.5 g, yield 97.5%.

G) Related compounds are readily made using similar techniques, including, but not limited to:

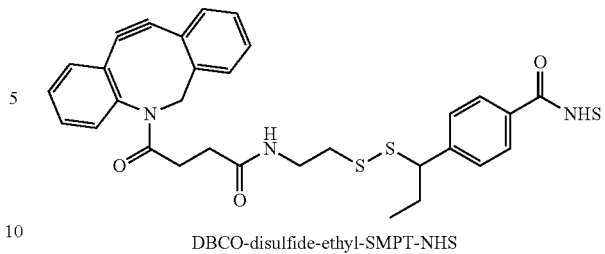

DBCO-disulfide-ethyl-SMPT-NHS

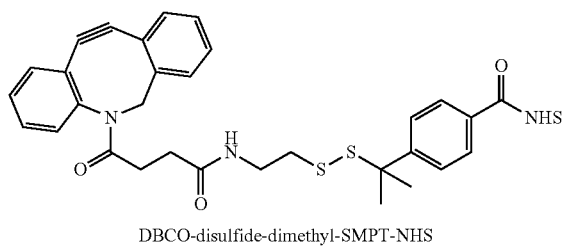

DBCO-disulfide-dimethyl-SMPT-NHS

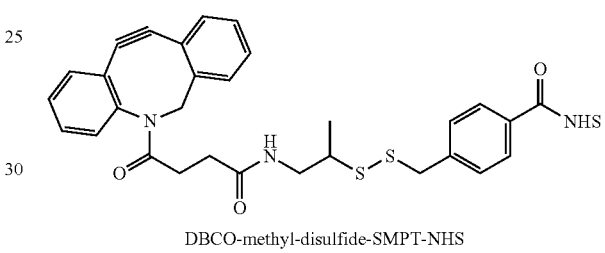

DBCO-methyl-disulfide-SMPT-NHS

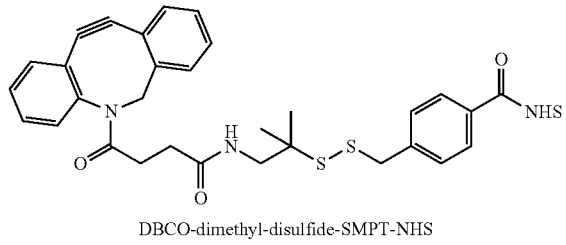

DBCO-dimethyl-disulfide-SMPT-NHS

Example 3

RNAi Agents Targeting the Factor VII Gene were Conjugated to Unbranched Linkers (AD0096), Methyl Branched Linkers (AD0919), or Dimethyl Branched Linkers (AD0920)

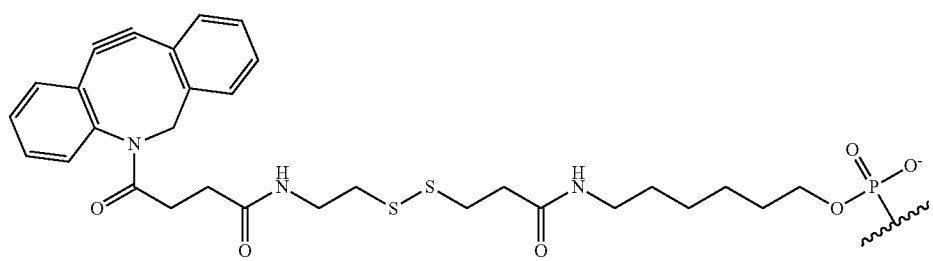

AD0096 (unbranched linker)
(The phosphate group can be part of the RNAi agent or RNAi reagent sense strand.)

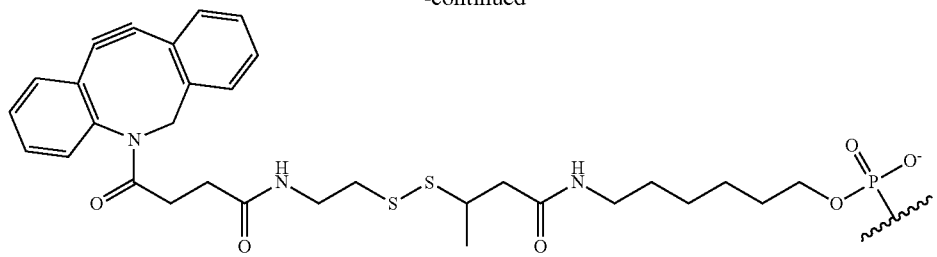

AD0919 (methyl branched linker)
(The phosphate group can be part of the RNAi agent or RNAi reagent sense strand.)

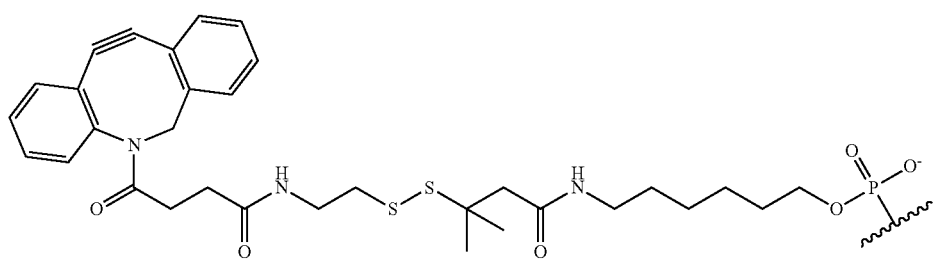

AD0920 (dimethyl branched linker)
(The phosphate group can be part of the RNAi agent or RNAi reagent sense strand.)

HPLC analyses (FIG. 7, 9, 10) showed significantly fewer impurities when using the branched linkers. Yields also improved.

A) Synthesis of DBCO-disulfide-RNAi Agent Conjugate

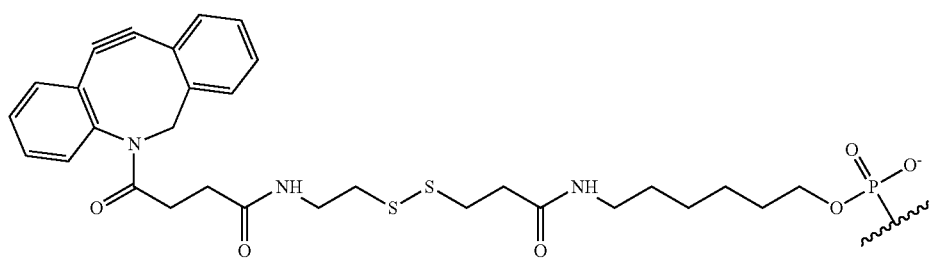

DBCO-disulfide-
(The phosphate group can be part of the RNAi agent or RNAi reagent sense strand.)

Figure 7:
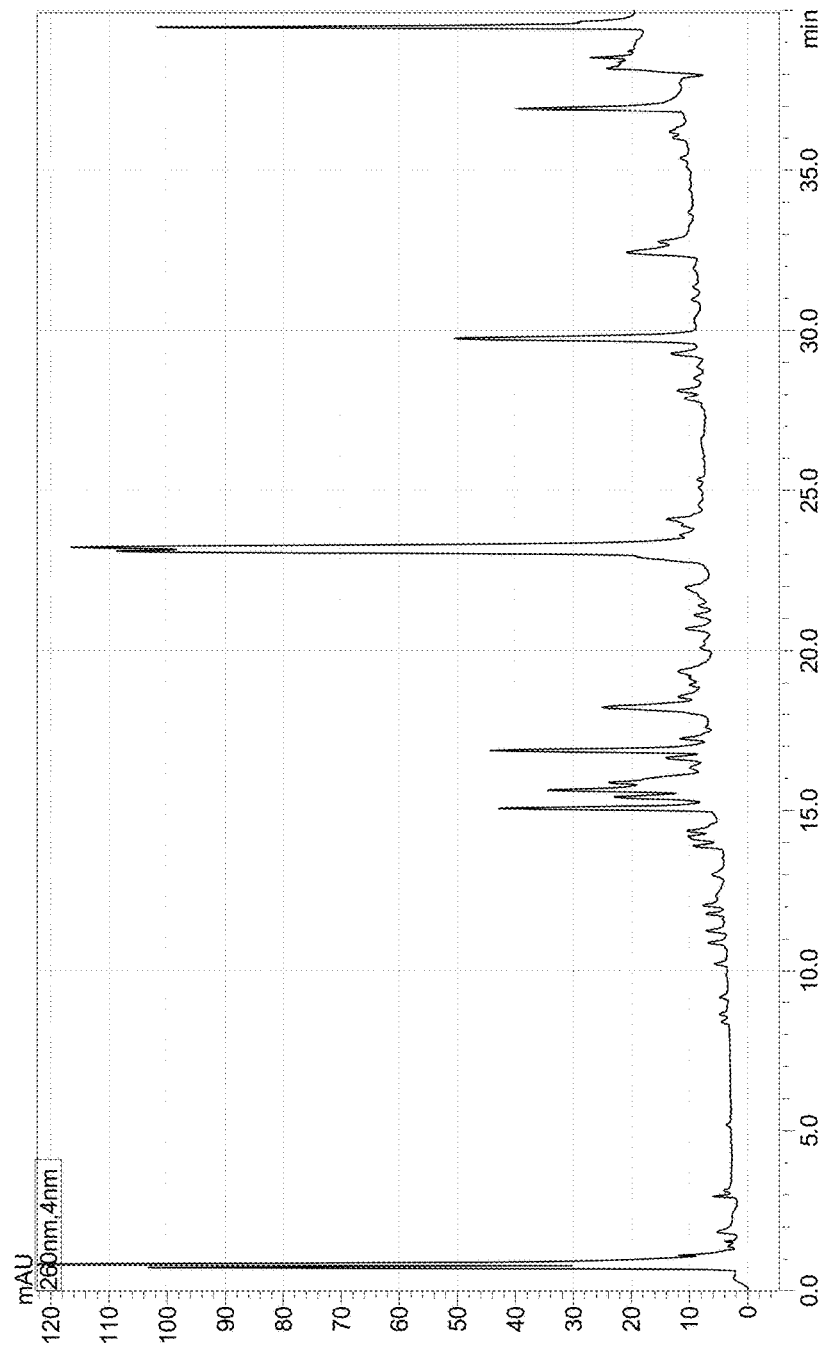
FIG. 7. RP-HPLC chromatogram of the reaction mixture of the RNAi agent sense strand conjugate prepared with an unbranched DBCO disulfide modifier (DBCO-disulfide-NHS ester).

Crude RNA (2.7 mg, 402 nmol) with a 5' C-6 amino modification, was precipitated using sodium acetate (0.5M) in EtOH, lyophilized, and dissolved in 442 µL 0.1M NaHCO$_3$, pH 8-9. Dibenzocyclooqyne-S—S—N-hyclroxy-succinimidyl ester (DBCO—SS—NHS) ester (2.3 mg, 4063.6 nmol) was dissolved in 227 µL DMF and added to the RNA solution. The reaction mixture was mixed well and allowed to proceed for 2 h at room temp. The reaction was monitored using RP-HPLC and the purity was determined upon reaction completion (purity 34.4%). After reaction completion, the reaction mixture was dried down and purified using RP-HPLC. The RNAi agent conjugate was prepared in 18% yield (75 nmol). The final purity of the RNAi agent conjugate was determined by RP-HPLC (purity: 92.4%) and the identity was confirmed by MALDI-TOF/TOF (Mass calculated: 7164.0; Mass observed: 7165.3). FIG. 7. RP-HPLC chromatogram of the reaction mixture of the RNAi agent conjugate prepared with DBCO-disulfide-NHS ester (AM00253-SS, 1141-66K_6).

B) Synthesis of DBCO-RNAi Agent Conjugate

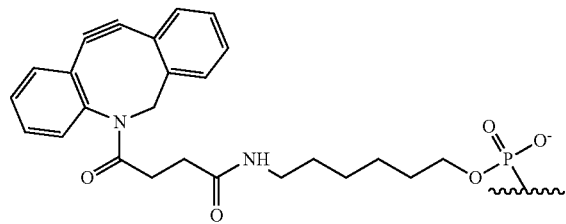

DBCO-
(The phosphate group can be part of the RNAi agent or RNAi reagent sense strand.)

Figure 8:
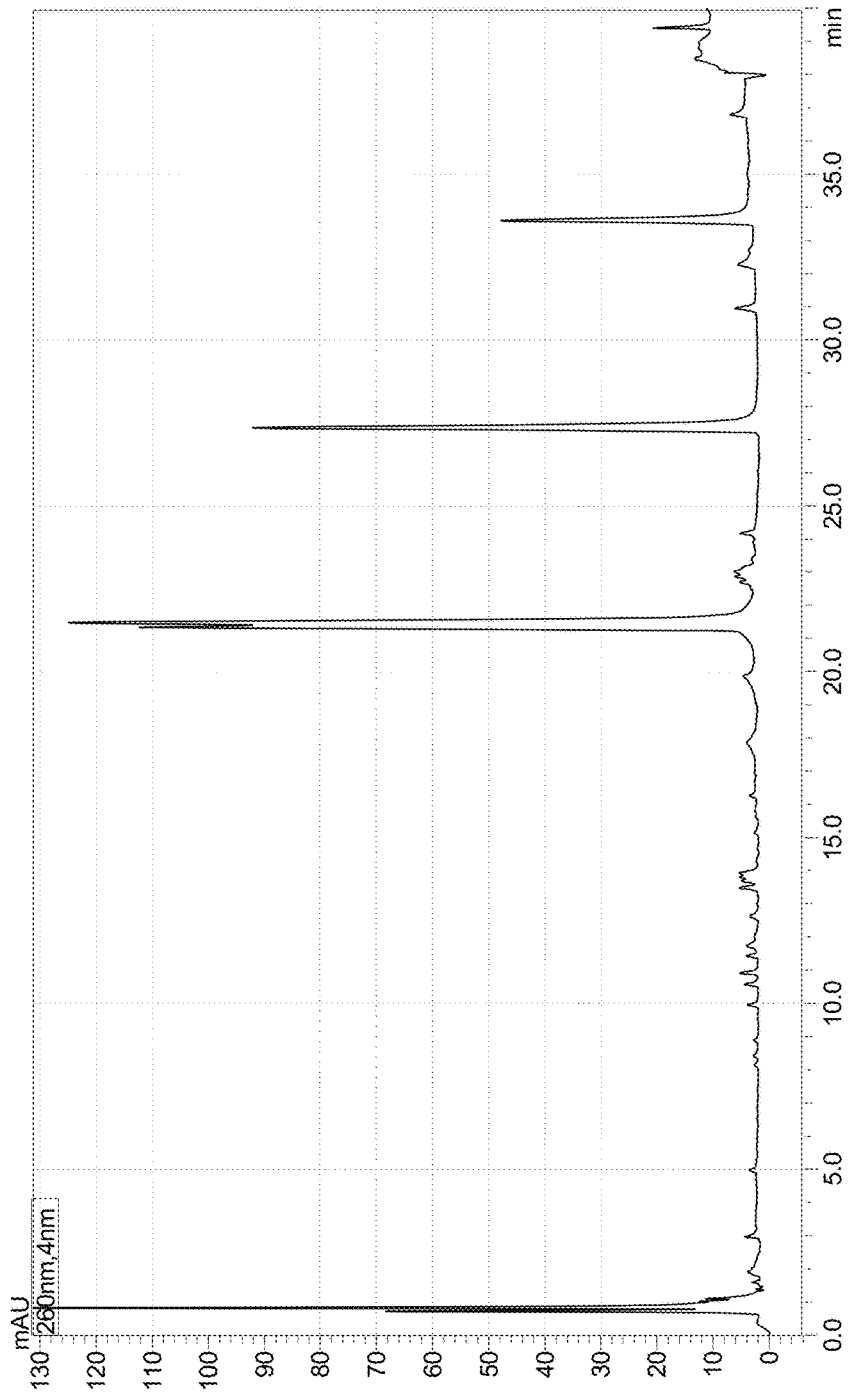
FIG. 8. RP-HPLC chromatogram of the reaction mixture of the RNAi agent conjugate prepared with DBCO—NHS ester.

RNAi agent conjugate was similarly prepared using a DBCO—NHS ester without the disulfide bond. The purity upon reaction completion was determined by RP-HPLC (purity: 54.0%). The RNAi agent conjugate was prepared in 60% yield (270 nmol). The final purity was determined by RP-HPLC (purity: 90.1%) and the identity was confirmed by MALDI-TOF/TOF (Mass calculated: 6999.3; Mass observed: 6998.7). FIG. 8. RP-HPLC chromatogram of the reaction mixture of the RNAi agent conjugate prepared with DBCO—NHS ester. (AM01707-SS, 1141-18K_1).

C) Synthesis of DBCO-disulfide-methyl-RNAi Agent Conjugate

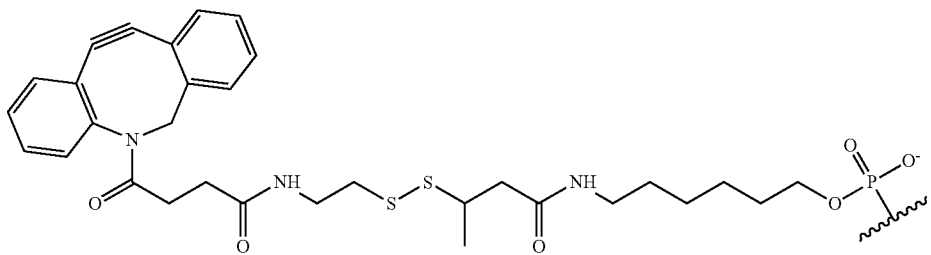

DBCO-disulfide-methyl-
(The phosphate group can be part of the RNAi agent or RNAi reagent sense strand.)

Figure 9:
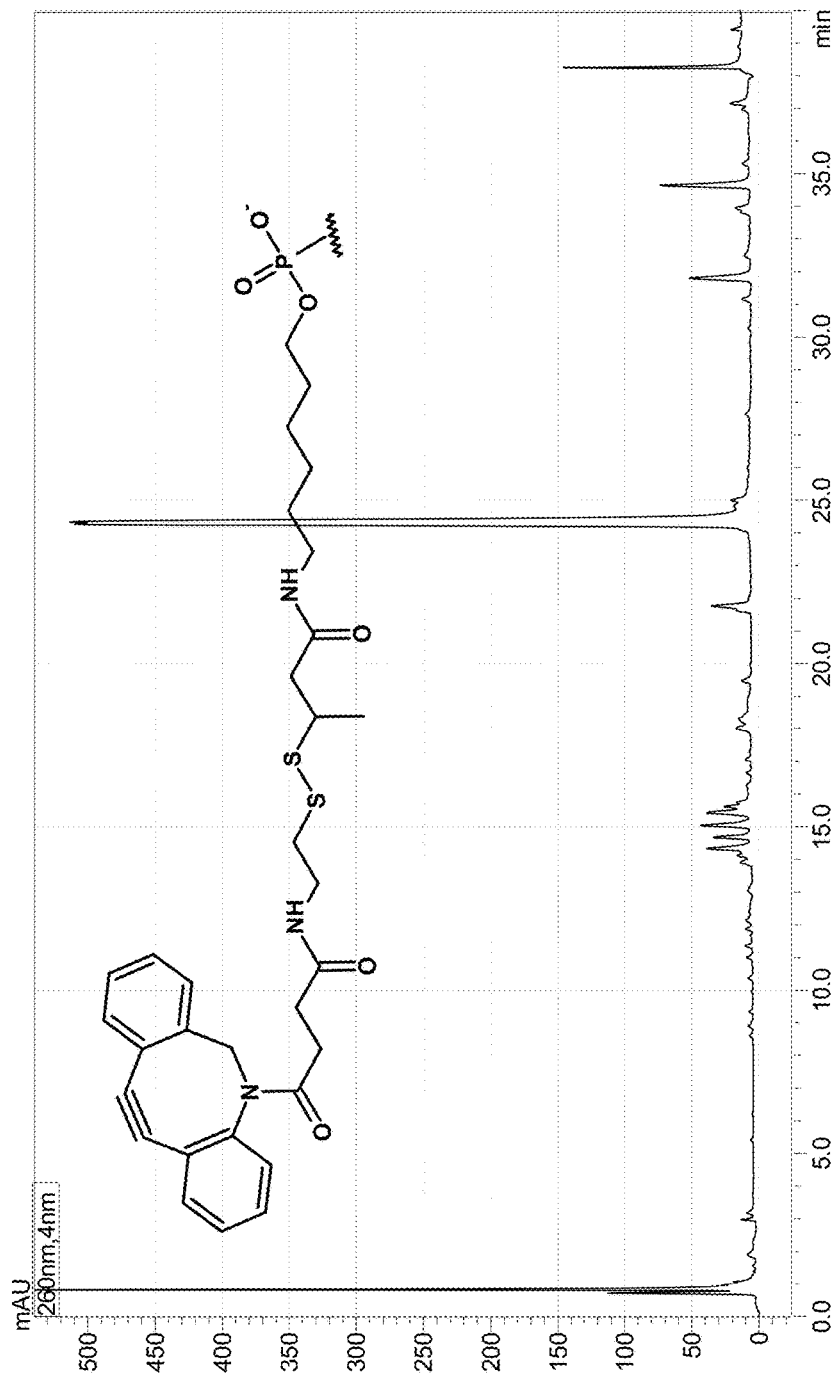
FIG. 9. RP-HPLC chromatogram of the reaction mixture of the RNAi agent sense strand conjugate prepared with DBCO-Alkane(methyl)-disulfide modifier.

RNAi agent conjugate was similarly prepared using a DBCO—SS-methyl-NHS ester with a methyl group stabilizing the disulfide bond. The purity upon reaction completion was determined by RP-HPLC (purity: 74.7%). The RNAi agent conjugate was prepared in 53% yield (1808 nmol). The final purity was determined by RP-HPLC (purity: 96.6%) and the identity was confirmed by MALDI-TOF/TOF (Mass calculated: 7191.3; Mass observed: 7191.7). FIG. 9. RP-HPLC chromatogram of the reaction mixture of the RNAi agent conjugate prepared with DBCO-disulfide-methyl-NHS. (AM01637-SS, 1141-11K_5)

D) Synthesis of DBCO-disulfide-dimethyl-RNAi Agent Conjugate

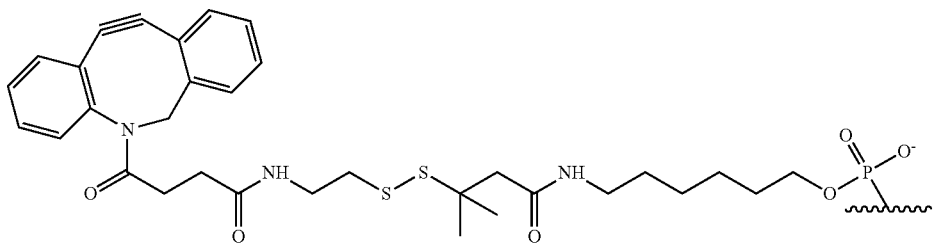

DBCO-disulfide-dimethyl-
(The phosphate group can be part of the RNAi agent or RNAi reagent sense strand.)

Figure 10:
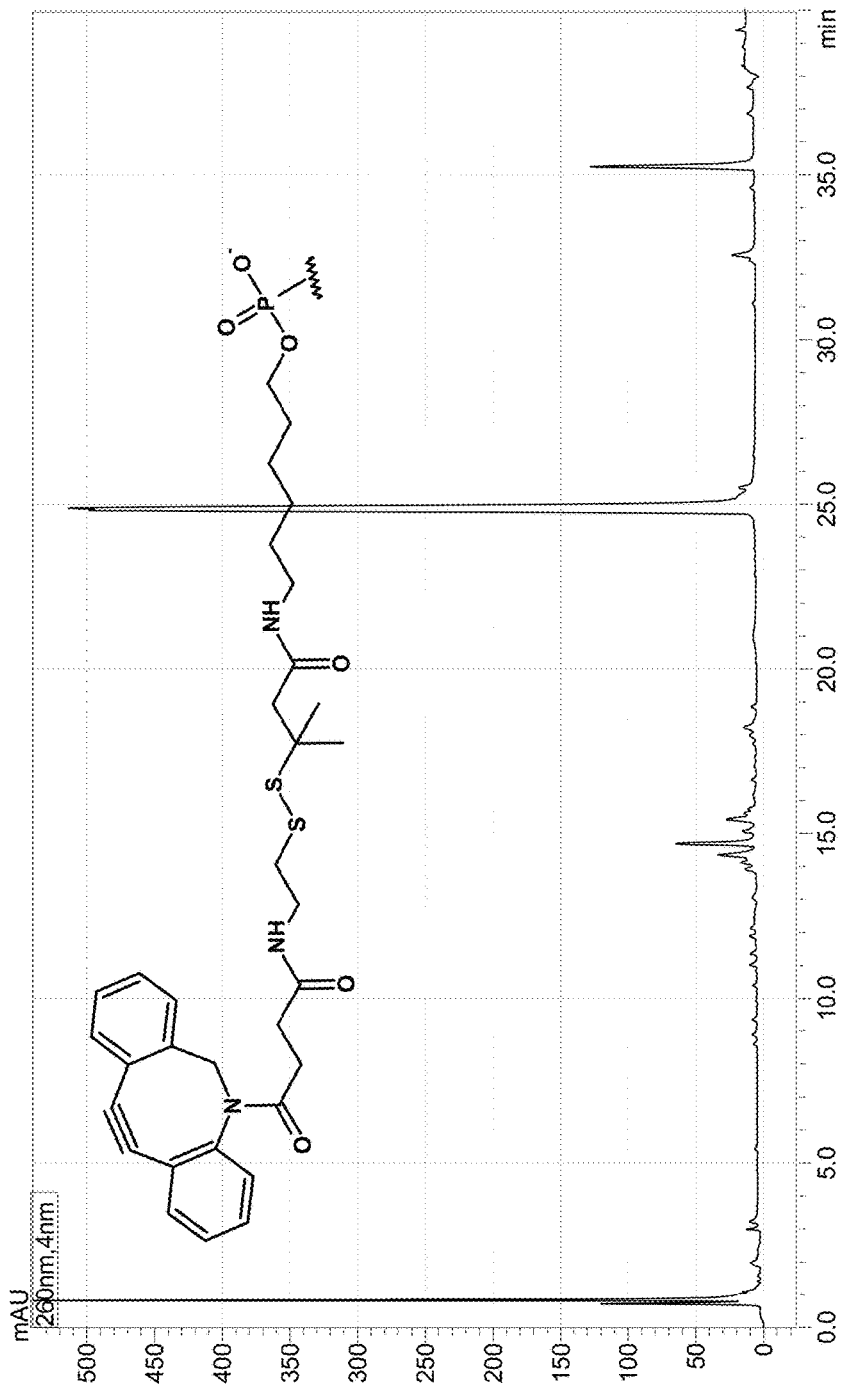
FIG. 10. RP-HPLC chromatogram of the reaction mixture of the RNAi agent sense strand conjugate prepared with Branched DBCO-Alkane(dimethyl)-disulfide modifier.

The RNAi agent conjugate was prepared using a DBCO-disulfide-dimethyl-NHS ester with two methyl groups stabilizing the disulfide bond. The purity upon reaction completion was determined by RP-HPLC (purity: 80.6%). The RNAi agent conjugate was prepared in 66% yield (2259 nmol). The final purity was determined by RP-HPLC (purity: 96.6%) and the identity was confirmed by MALDI-TOF/TOF (Mass calculated: 7205.3; Mass observed: 7204.9). FIG. 10. RP-HPLC chromatogram of the reaction mixture of the RNAi agent conjugate prepared with the DBCO-disulfide-dimethyl-NHS (AM01638-SS, 1141-11K_4).

E) Synthesis of DBCO-disulfide-methyl-SMPT-RNAi Agent Conjugate

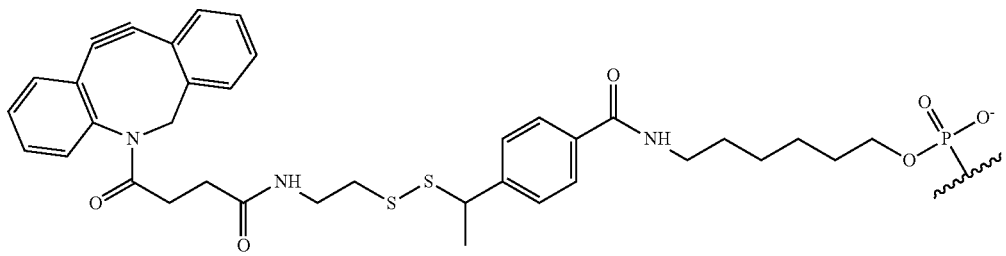

DBCO-disulfide-methyl-SMPT-
(The phosphate group can be part of the RNAi agent or RNAi reagent sense strand.)

Figure 11:
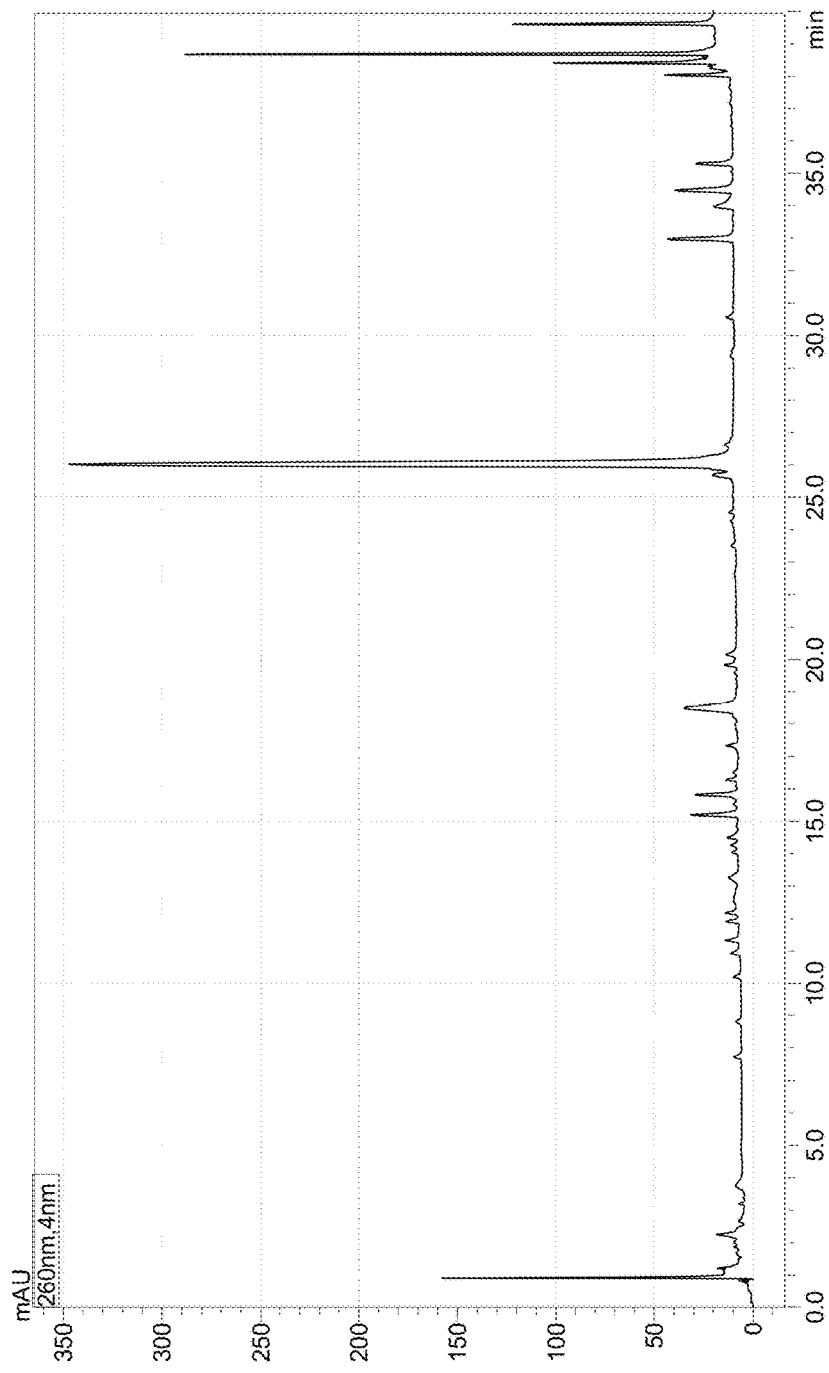
FIG. 11. RP-HPLC chromatogram of the reaction mixture of the RNAi agent conjugate prepared with the DBCO-disulfide-methyl-SMPT.
Figure 12:
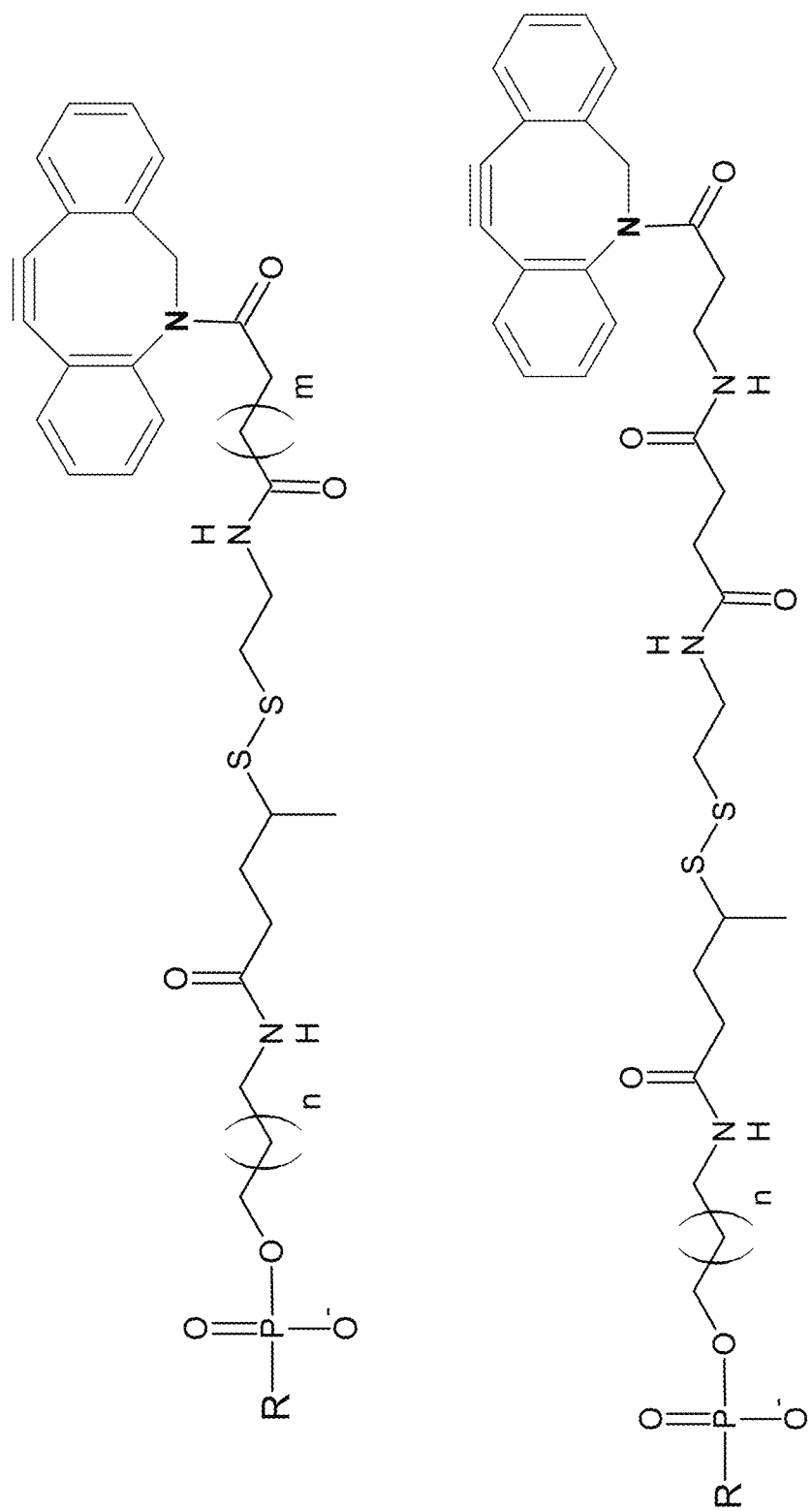
FIG. 12. Disclosed embodiments of certain cyclooctyne-alkyl-S—S-oligonucleotide compounds R comprises an oligonucleotide or RNAi agent. The phosphate groups shown may be part of a synthetic oligonucleotide or RNAi agent.

The RNAi agent conjugate was prepared using DBCO-disulfide-methyl-SMPT. The purity upon reaction completion was determined by RP-HPLC (purity: 72.7%) The RNAi agent conjugate was prepared in 35% yield (1050 nmol). The final purity was determined by RP-HPLC (purity: 96.6%) and the identity was confirmed by MALDI-TOF/TOF (Mass calculated: 7238.3; Mass observed: 7238.3). FIG. 11. RP-HPLC chromatogram of the reaction mixture of the RNAi agent conjugate prepared with the DBCO-disulfide-methyl-SMPT (AM02455-SS, 1183-61K_2).

TABLE 1

Summary of the reaction mixture purity and percent yield using five different modifiers.

| Type of Modifier | Reaction Mixture Purity | Percent Yield after Purification |
|---|---|---|
| DBCO-disulfide-NHS | 34.4 | 18.8 |
| DBCO-NHS | 54.0 | 60.3 |
| DBCO-disulfide-methyl-NHS | 74.7 | 52.8 |
| DBCO-disulfide-dimethyl-NHS | 80.6 | 65.9 |
| DBCO-disulfide-methyl-SMPT | 72.7 | 35.4 |

In stabilizing the disulfide bond, the RNAi agent conjugate can be prepared with greater purity before purification, allowing for a greater reaction yield.

LC showed decreased impurities using branched linkers (DBCO conjugated to RNAi agent)

AD0096

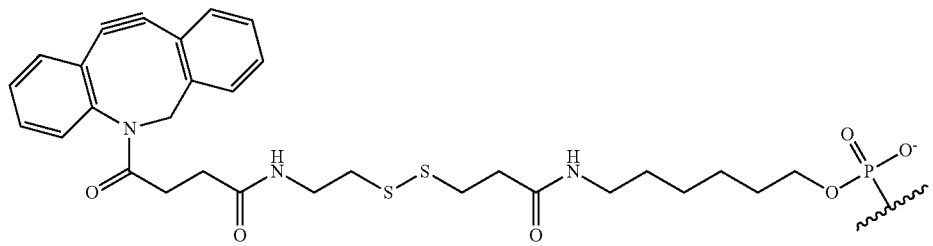

(unbranched linker)
(The phosphate group can be part of the RNAi agent or RNAi reagent sense strand.)

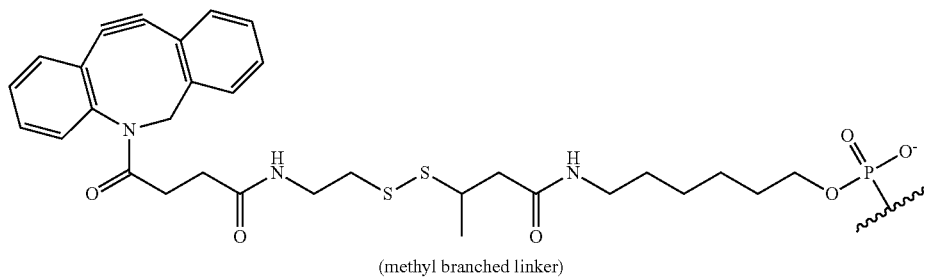

AD0919

(methyl branched linker)
(The phosphate group can be part of the RNAi agent or RNAi reagent sense strand.)

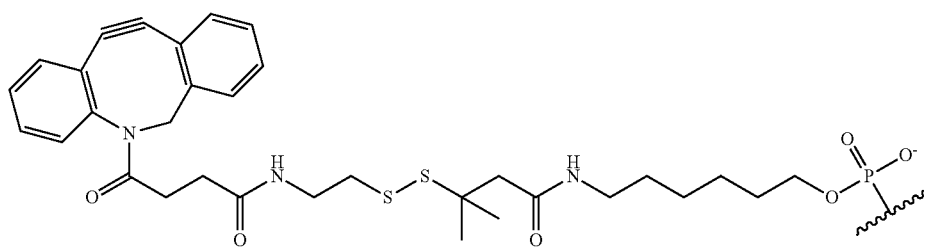

AD0920

(dimethyl branched linker)
(The phosphate group can be part of the RNAi agent or RNAi reagent sense strand.)

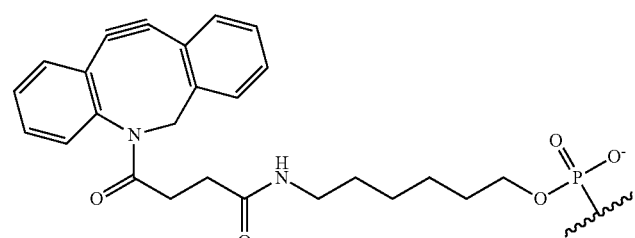

AD0921

(The phosphate group can be part of the RNAi agent or RNAi reagent sense strand.)

Example 4

In Vivo Effectiveness of Alkyne-disulfide-alkyl Modifiers

A) RNAi agents. of the following sequences were synthesized using standard phosphoramidite chemistry with C6 amino linker at the 5' end of the sense strand added using commercially-available 6-(4-Monomethoxytritylamino)hexyl-(2-cyanoethyl)-(N,N-diisopropyl)-phosphoramidite (from Glen Research).

TABLE 2

Factor VII RNAi agents

| Duplex ID | strand | SEQ ID | Sequence 5' → 3' |
|---|---|---|---|
| AD0096 | Antisense | 1 | dTsGfaGfuUfgGfcAfcGfcCfuUfuGfcdTsdT |
|  | Sense | 2 | (DBCO-SS-C6)GfcAfaAfgGfcGfuGfcCfaAfcUfcAf(invdT) |
| AD0919 | Antisense | 3 | dTsGfaGfuUfgGfcAfcGfcCfuUfuGfcdTsdT |
|  | Sense | 4 | (DBCO-SS-methyl-C6)GfcAfaAfgGfcGfuGfcCfaAfcUfcAf(invdT) |
| AD0920 | Antisense | 5 | dTsGfaGfuUfgGfcAfcGfcCfuUfuGfcdTsdT |
|  | Sense | 6 | (DBCO-SS-dimethyl-C6)GfcAfaAfgGfcGfuGfcCfaAfcUfcAf(invdT) |
| AD0921 | Antisense | 4 | dTsGfaGfuUfgGfcAfcGfcCfuUfuGfcdTsdT |
|  | Sense | 8 | (DBCO-C6)GfcAfaAfgGfcGfuGfcCfaAfcUfcAf(invdT) |

TABLE 2-continued

Factor VII RNAi agents

| Duplex ID | strand | SEQ ID | Sequence 5' → 3' |
|---|---|---|---|
| AD1477 | Antisense | 9 | dTsGfaGfuUfgGfcAfcGfcCfuUfuGfcdTsdT |
|  | Sense | 10 | (DBCO-SS-methyl-SMPT-C6)GfcAfaAfgGfcGfuGfcCfaAfcUfcAf(invdT) | n (lower case) = 2'-OMe substitution nucleotide
Nf = 2'-Fluoro nucleotide
dN = 2-deoxy substitution;
inv = 3' to 3' linkage
s = phosphorothioate linkage B) RAFT copolymer of N-Boc-ethoxyethylamine acrylate and sec-butyl acrylate (EAB). Solutions of AIBN (1.00 mg/mL) and RAFT agent CPCPA (10.0 mg/mL) in butyl acetate were prepared. Monomer molar feed was 55% N-Boc-ethoxyethylamine acrylate, 45% sec-butyl acrylate (CAS #2998-08-5). Theoretical Mw was 100,000.

N-Boc-ethoxyethylamine acrylate (0.890 g, 3.43 mmol) sec-butyl acrylate (0.391 mL, 0.360 g, 2.81 mmol) CPCPA solution (0.350 mL, 0.0125 mmol), AIBN solution (0.308 mL, 0.00188 mmol), and butyl acetate (5.3 mL) were added to a 20 mL glass vial with stir bar. The vial was sealed with a septa cap and the solution bubbled with nitrogen using a long syringe with a second syringe as the outlet for 1 h. The syringes were removed and the vial heated to 80° C. for 16 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (40 mL) and centrifuged once more. The supernatant was decanted and the bottom layer rinsed with hexane before the polymer was dried under reduced pressure for several hours. Yield of crude EAB copolymer was 0.856 g. Samples of the crude polymer were taken for multi-angle light scattering (MALS). The dried, crude copolymer was dissolved in DCM (100 mg/mL). Hexane was added until just after the cloud point was reached. The resulting milky solution was centrifuged. The bottom layer was extracted and fully precipitated into hexane. The fraction was centrifuged, after which the copolymer was isolated and dried under vacuum. Yield of isolated fraction of EAB copolymer was 0.478 g. Samples of the fractionated copolymer were taken for $^1$H-NMR and MALS. Composition determined by $^1$H-NMR was 61% N-Boc-ethoxyethylamine and acrylate, 39% sec-butyl acrylate.

MALS Analysis. Approximately 10 mg of the copolymer was dissolved in 0.5 mL 75% dichloromethane, 20% tetrahydrofuran, 5% acetonitrile. The molecular weight and polydispersity (PDI) were measured using a Wyatt Heleos II multiangle light scattering detector attached to a Shimadzu Prominence HPLC using a Jordi 5μ 7.8×300 Mixed Bed LS DVB column. Crude Polymer: MW: 59,000 (PDI 1.3), Fractionated Polymer: MW 70,000 (PDI: 1.1).

Deprotection/Dialysis. The dried samples were treated with 2M HCl in acetic acid (~7 ml) for 1 h to remove the BOC protecting groups. Then the reaction was diluted with 20 mL of water and allowed to stir for 10-15 min. The fractions were then dialyzed with 3500 MW dialysis tubing in high salt, high salt, and water for 15 h, 8 h, and 15 h respectively. The fractions were then transferred to 50 mL centrifuge tubes and lyophilized for 3 days or until dry. The dry samples were brought up at 20 mg/mL in water for further study.

RNAi agent-polymer formulations. Polyacrylate EAB in 5 mM pH 8.0 HEPES buffer was modified 1.5 wt % with a N-hydroxysuccinimidyl activated $PEG_4$ azide (Azido-$dPEG_4$-NHS ester from Quanta Biodesign) to provide azide groups for subsequent attachment of RNAi agent. The azide-modified polymer was then diluted to 5 mg/mL in 60 mg/mL HEPES base. To this solution was added 15 mg/mL (3 wt equivalents) PEG masking reagent PEG-Ala-Cit-PABC to modify 40-50% of available amine groups. After 1 h, DBCO-modified rodent Factor VII RNAi agent (0.125 wt eq relative to polymer) was added to polymer solution. After incubation overnight, conjugates were further modified by addition of molar excess relative to available amine groups of an N-acetylgalactosamine derivative NAG-Ala-Cit-PABC (presented in Table 2), and incubated for 30 minutes.

Mice and injection procedures. Female ICR mice, 6 to 8 weeks old, were obtained from Harlan Sprague-Dawley, (Indianapolis, Ind.). All the mice were handled in accordance with animal used protocols approved by the Animal Care and Use Committee at Arrowhead Madison Inc. Rodents were maintained on a 12 h light/dark cycle with free access to water and food (Harlan Teklad Rodent Diet, Harlan, Madison, Wis.). Delivery formulations were injected as a bolus into the tail vein in a total volume of 0.2 mL (mice) or HEPES-buffered (5 mM, pH 7.5) isotonic glucose under standard conditions. Mice were injected with 2 mg/kg polymer conjugated to 0.25 mg/kg RNAi agent. Serum samples collected 5 days post-injection.

Serum FVII activity measurements. Serum samples were prepared by collecting blood by submandibular bleeding into microcentrifuge tubes containing 0.109 M sodium citrate anticoagulant (1 volume) following standard procedures. FVII activity in serum was measured with a chromogenic method using a test kit (BIOPHEN VII, Aniara, Mason, Ohio) following manufacturer's recommendations. Absorbance of colorimetric development was measured using a Tecan Safire-2 microplate reader at 405 nm.

TABLE 3

Normalized Factor VII levels after injection of polymer-RNAi agent disulfide conjugates.

| DBCO disulfide | Relative F VII activity |
|---|---|
| EAB-RNA | 91 ± 15 |
| EAB-SS-RNA | 16 ± 7 |
| EAB-SS-methyl-RNA | 12 ± 7 |
| EAB-SS-dimethyl-RNA | 36 ± 10 |
| EAB-S-S-methyl-SMPT-RNA | 26 ± 7 |

The invention claimed is:

1. An RNAi agent-containing compound for inhibiting the expression of a target gene in a cell in vitro or in vivo, the RNAi agent-containing composition comprising an RNAi agent covalently linked to an cyclooctyne-alkyl disulfide compound, the RNAi agent-containing compound having the structure represented by:

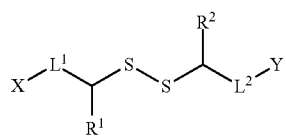

wherein,

R¹ is an alkyl group and R² is hydrogen, or R¹ is hydrogen and R² is an alkyl group, L¹ and L² are linkers, X comprises a cyclooctyne, and Y comprises an RNAi agent.

2. The RNAi agent-containing compound of claim 1, wherein the alkyl group is a methyl group.

3. The RNAi agent-containing compound of claim 1, wherein X is diarylcyclooctyne, DBCO, Azadibenzocyclooctyne (DIBAC or ADIBO),

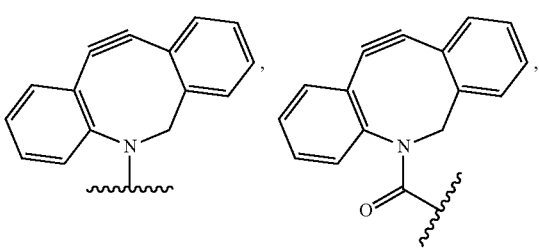

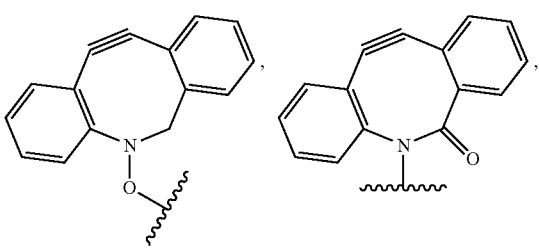

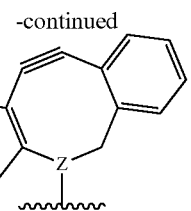

wherein Z=C or N,

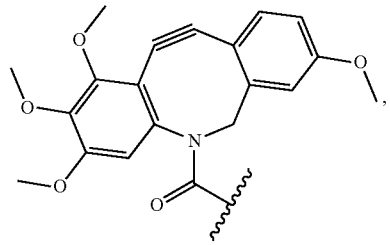

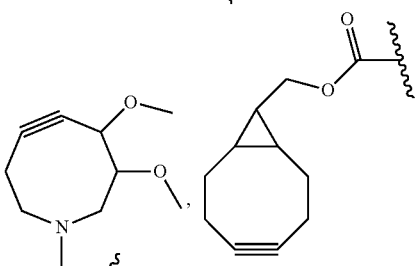

, or

.

4. The RNAi agent-containing compound of claim 1, further including one or more pharmaceutically acceptable excipients.

5. The RNAi agent-containing compound of claim 1, wherein the RNAi agent is an siRNA.

6. An RNAi agent-containing compound for inhibiting the expression of a target gene in a cell in vitro or in vivo, the RNAi agent-containing compound comprising an RNAi agent covalently linked to an cyclooctyne-alkyl disulfide compound, the RNAi agent-containing compound having the structure represented by:

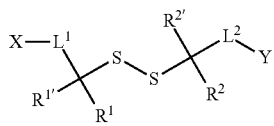

wherein
R¹ and R¹' are each alkyl groups and R² and R²' are each hydrogen, or R¹ and R¹' are each hydrogen and R² and R²' are each alkyl groups,
L¹ and L² are linkers,
X comprises a cyclooctyne, and
Y comprises an RNAi agent.

7. The RNAi agent-containing compound of claim 6, wherein the alkyl groups are methyl groups.

8. The RNAi agent-containing compound of claim 6, wherein X is diarylcyclooctyne, DBCO, Azadibenzocyclooctyne (DIBAC or ADIBO),

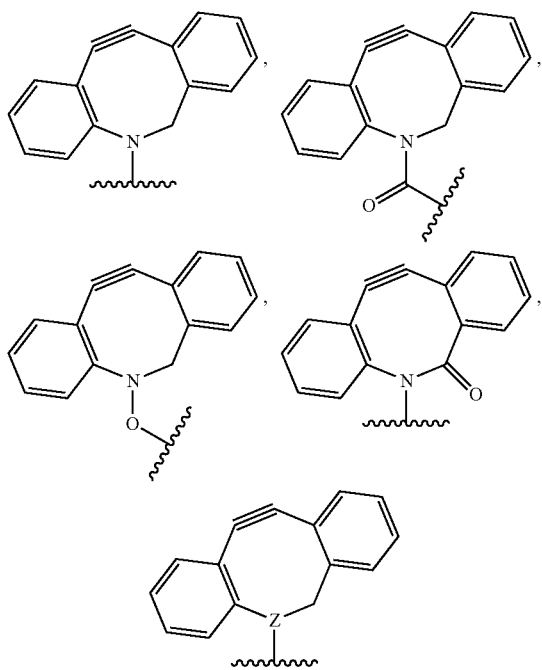

wherein Z=C or N,

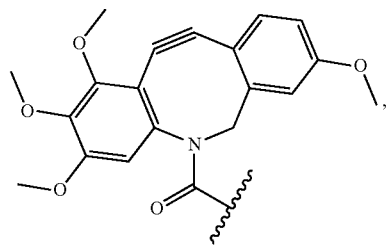

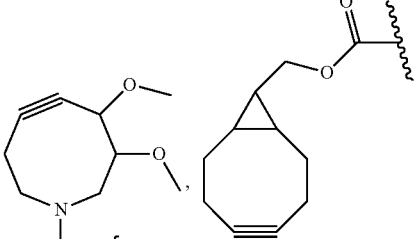

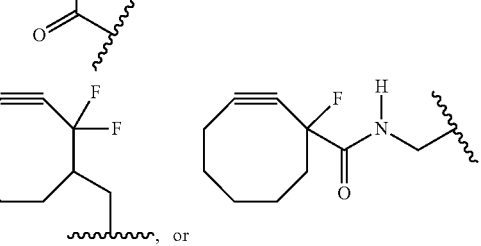

, or

9. The RNAi agent-containing compound of claim 6, further including one or more pharmaceutically acceptable excipients.

10. The RNAi agent-containing compound of claim 6, wherein the RNAi agent is an siRNA.

11. A method of inhibiting the expression of a target gene in a cell, the method comprising delivering to the cell an effective amount of the RNAi agent-containing compound of claim 1.

12. A method of inhibiting the expression of a target gene in a cell, the method comprising delivering to the cell an effective amount of the RNAi agent-containing compound of claim 6.

* * * * *